United States Patent
Mason et al.

(10) Patent No.: US 11,410,768 B2
(45) Date of Patent: Aug. 9, 2022

(54) METHOD AND SYSTEM FOR IMPLEMENTING DYNAMIC TREATMENT ENVIRONMENTS BASED ON PATIENT INFORMATION

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM TECHNOLOGIES, INC., Brookfield, CT (US)

( * ) Notice: Subject to any disclaimer, the term of this patent is extended or adjusted under 35 U.S.C. 154(b) by 0 days.

(21) Appl. No.: 17/379,661

(22) Filed: Jul. 19, 2021

(65) Prior Publication Data
US 2021/0350902 A1 Nov. 11, 2021

Related U.S. Application Data

(63) Continuation of application No. 17/147,232, filed on Jan. 12, 2021, which is a continuation-in-part of
(Continued)

(51) Int. Cl.
*A63B 22/06* (2006.01)
*G16H 20/40* (2018.01)
(Continued)

(52) U.S. Cl.
CPC ......... *G16H 20/40* (2018.01); *A63B 22/0605* (2013.01); *G16H 10/60* (2018.01); *G16H 40/67* (2018.01); *A63B 2022/0629* (2013.01)

(58) Field of Classification Search
CPC .................. A61H 1/0214; A61H 1/024; A61H 2201/1215; A61H 2201/1261;
(Continued)

(56) References Cited

U.S. PATENT DOCUMENTS

| 59,915 A | 11/1866 | Lallement |
|---|---|---|
| 363,522 A | 5/1887 | Knous |

(Continued)

FOREIGN PATENT DOCUMENTS

| CA | 2698078 A1 | 3/2010 |
|---|---|---|
| CN | 112603295 A | 2/2003 |

(Continued)

OTHER PUBLICATIONS

International Searching Authority, Search Report and Written Opinion for International Application No. PCT/US20/51008, dated Dec. 10, 2020; 8 pages.

(Continued)

*Primary Examiner* — George Manuel
(74) *Attorney, Agent, or Firm* — Dickinson Wright, PLLC; Stephen A. Mason; Jonathan H. Harder

(57) ABSTRACT

A system that comprises a memory device storing instructions, and a processing device communicatively coupled to the memory device. The processing device executes the instructions to: receive user data obtained from records associated with a user; generate a modified treatment plan based on the user data; and send, to a treatment apparatus accessible to the user, the modified treatment plan, wherein the modified treatment plan causes the treatment apparatus to update at least one operational aspect of the treatment apparatus, and update at least one operational aspect of at least one other device communicatively coupled to the treatment apparatus.

18 Claims, 17 Drawing Sheets

Related U.S. Application Data application No. 17/021,895, filed on Sep. 15, 2020, now Pat. No. 11,071,597.

(60) Provisional application No. 62/910,232, filed on Oct. 3, 2019.

(51) Int. Cl.
*G16H 10/60* (2018.01)
*G16H 40/67* (2018.01)

(58) Field of Classification Search
CPC ........ A61H 2201/164; A61H 2201/501; A61H 2201/5043; A61H 2201/5061; A61H 2201/5064; A61H 2201/5069; A61H 2201/5071; A61H 2201/5092; A61H 2201/5097; A61H 2203/0431; A61H 2205/10; A63B 2022/0094; A63B 2022/0623; A63B 2022/0629; A63B 2071/0625; A63B 2071/063; A63B 2071/0675; A63B 2071/068; A63B 2220/10; A63B 2220/16; A63B 2220/17; A63B 2220/20; A63B 2220/30; A63B 2220/51; A63B 2220/52; A63B 2220/80; A63B 2220/806; A63B 2220/808; A63B 2220/833; A63B 2225/09; A63B 2225/093; A63B 2225/20; A63B 2225/50; A63B 2230/06; A63B 2230/30; A63B 2230/42; A63B 2230/50; A63B 22/0605; A63B 22/0694; A63B 71/0622; A63B 10/60; G16H 10/60; G16H 20/30; G16H 20/40; G16H 40/67; G16H 50/70

See application file for complete search history.

(56) References Cited

U.S. PATENT DOCUMENTS

| | | |
|---|---|---|
| 446,671 A | 2/1891 | Elliot |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorfp |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |
| 4,961,570 A | 10/1990 | Chang |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,474,193 B1 | 11/2002 | Farney |
| 6,491,649 B1 | 12/2002 | Ombrellaro |
| 6,535,861 B1 | 3/2003 | OConnor et al. |
| 6,543,309 B2 | 4/2003 | Heim |
| 6,589,139 B1 | 7/2003 | Butterworth |
| 6,602,191 B2 | 8/2003 | Quy |
| 6,626,805 B1 | 9/2003 | Lightbody |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 7,156,665 B1 | 1/2007 | OConnor et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,507,188 B2 | 3/2009 | Nurre |
| 7,594,879 B2 | 9/2009 | Johnson |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,974,689 B2 | 7/2011 | Volpe et al. |
| 8,079,937 B2 | 12/2011 | Bedell et al. |
| 8,287,434 B2 | 10/2012 | Zavadsky et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,672,812 B2 | 3/2014 | Dugan |
| 8,751,264 B2 | 6/2014 | Beraja et al. |
| 8,784,273 B2 | 7/2014 | Dugan |

(56) References Cited

U.S. PATENT DOCUMENTS

| | | |
|---|---|---|
| 8,823,448 B1 | 9/2014 | Shen |
| 8,979,711 B2 | 3/2015 | Dugan |
| D744,050 S | 11/2015 | Colburn |
| 9,248,071 B1 | 2/2016 | Benda et al. |
| 9,272,185 B2 | 3/2016 | Dugan |
| 9,283,434 B1 | 3/2016 | Wu |
| 9,311,789 B1 | 4/2016 | Gwin |
| 9,409,054 B2 | 8/2016 | Dugan |
| 9,443,205 B2 | 9/2016 | Wall |
| 9,480,873 B2 | 11/2016 | Chuang |
| 9,481,428 B2 | 11/2016 | Gros et al. |
| 9,566,472 B2 | 2/2017 | Dugan |
| 9,579,056 B2 | 2/2017 | Rosenbek et al. |
| 9,629,558 B2 | 4/2017 | Yuen et al. |
| D794,142 S | 8/2017 | Zhou |
| 9,717,947 B2 | 8/2017 | Lin |
| 9,737,761 B1 | 8/2017 | Govindarajan |
| 9,782,621 B2 | 10/2017 | Chiang et al. |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,155,134 B2 | 12/2018 | Dugan |
| 10,159,872 B2 | 12/2018 | Sasaki et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,226,663 B2 | 3/2019 | Gomberg et al. |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| 10,792,495 B2 | 10/2020 | Izvorski et al. |
| 10,874,905 B2 | 12/2020 | Belson et al. |
| D907,143 S | 1/2021 | Ach et al. |
| 10,918,332 B2 | 2/2021 | Belson et al. |
| 10,931,643 B1 | 2/2021 | Neumann |
| 11,000,735 B2 | 5/2021 | Orady et al. |
| 11,045,709 B2 | 6/2021 | Putnam |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,644 S | 12/2021 | Ach et al. |
| D940,797 S | 1/2022 | Ach et al. |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 2002/0072452 A1 | 6/2002 | Torkelson |
| 2002/0160883 A1 | 10/2002 | Dugan |
| 2003/0036683 A1 | 2/2003 | Kehr et al. |
| 2003/0064863 A1 | 4/2003 | Chen |
| 2003/0092536 A1 | 5/2003 | Romanelli et al. |
| 2003/0109814 A1 | 6/2003 | Rummerfield |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0147969 A1* | 7/2004 | Mann .................... G16H 20/30 607/17 |
| 2004/0172093 A1 | 9/2004 | Rummerfield |
| 2004/0194572 A1 | 10/2004 | Kim |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0274220 A1 | 12/2005 | Reboullet |
| 2006/0003871 A1 | 1/2006 | Houghton |
| 2006/0064329 A1 | 3/2006 | Abolfathi et al. |
| 2006/0247095 A1 | 11/2006 | Rummerfield |
| 2007/0042868 A1 | 2/2007 | Fisher et al. |
| 2007/0137307 A1 | 6/2007 | Gruben et al. |
| 2007/0173392 A1 | 7/2007 | Stanford |
| 2007/0287597 A1 | 12/2007 | Cameron |
| 2008/0021834 A1 | 1/2008 | Holla et al. |
| 2008/0153592 A1 | 6/2008 | James-Herbert |
| 2008/0161166 A1 | 7/2008 | Lo |
| 2008/0300914 A1 | 12/2008 | Karkanias et al. |
| 2009/0011907 A1 | 1/2009 | Radow et al. |
| 2009/0058635 A1* | 3/2009 | LaLonde ................ A61B 5/747 340/539.11 |
| 2009/0070138 A1 | 3/2009 | Langheier et al. |
| 2009/0211395 A1 | 8/2009 | Mul'e |
| 2009/0270227 A1 | 10/2009 | Ashby et al. |
| 2010/0048358 A1 | 2/2010 | Tchao et al. |
| 2010/0173747 A1 | 7/2010 | Chen et al. |
| 2010/0248899 A1 | 9/2010 | Bedell et al. |
| 2010/0248905 A1 | 9/2010 | Lu |
| 2010/0268304 A1 | 10/2010 | Matos |
| 2011/0047108 A1 | 2/2011 | Chakrabarty et al. |
| 2011/0172059 A1 | 7/2011 | Watterson et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0295240 A1 | 11/2012 | Walker et al. |
| 2012/0310667 A1 | 12/2012 | Altman et al. |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0296987 A1 | 11/2013 | Rogers et al. |
| 2013/0318027 A1 | 11/2013 | Almogy et al. |
| 2014/0006042 A1 | 1/2014 | Keefe et al. |
| 2014/0011640 A1 | 1/2014 | Dugan |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |

(56) References Cited

U.S. PATENT DOCUMENTS

| | | |
|---|---|---|
| 2014/0315689 A1 | 10/2014 | Vauquelin et al. |
| 2014/0322686 A1 | 10/2014 | Kang |
| 2015/0045700 A1 | 2/2015 | Cavanagh et al. |
| 2015/0088544 A1 | 3/2015 | Goldberg |
| 2015/0151162 A1 | 6/2015 | Dugan |
| 2015/0158549 A1 | 6/2015 | Gros et al. |
| 2015/0161331 A1 | 6/2015 | Oleynik |
| 2015/0290061 A1 | 10/2015 | Stafford et al. |
| 2015/0339442 A1 | 11/2015 | Oleynik |
| 2015/0379232 A1 | 12/2015 | Mainwaring et al. |
| 2016/0007885 A1 | 1/2016 | Basta et al. |
| 2016/0023081 A1 | 1/2016 | Popa-Simil |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2017/0004260 A1 | 1/2017 | Moturu et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0266501 A1 | 9/2017 | Sanders et al. |
| 2017/0278209 A1 | 9/2017 | Olsen et al. |
| 2017/0282015 A1 | 10/2017 | Wicks et al. |
| 2017/0300654 A1 | 10/2017 | Stein et al. |
| 2017/0312614 A1 | 11/2017 | Tran et al. |
| 2017/0329917 A1 | 11/2017 | McRaith et al. |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0052962 A1 | 2/2018 | Van Der Koijk et al. |
| 2018/0056104 A1 | 3/2018 | Cromie et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0263530 A1 | 9/2018 | Jung |
| 2018/0271432 A1 | 9/2018 | Auchinleck et al. |
| 2018/0280784 A1 | 10/2018 | Romeo et al. |
| 2018/0296157 A1 | 10/2018 | Bleich et al. |
| 2018/0330058 A1 | 11/2018 | Bates |
| 2018/0330824 A1 | 11/2018 | Athey et al. |
| 2018/0360340 A1 | 12/2018 | Rehse et al. |
| 2018/0373844 A1 | 12/2018 | Ferrandez-Escamez et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0060708 A1 | 2/2019 | Fung |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0111299 A1 | 4/2019 | Radcliffe et al. |
| 2019/0115097 A1 | 4/2019 | Macoviak et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0200920 A1 | 7/2019 | Tien et al. |
| 2019/0209891 A1 | 7/2019 | Fung |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0290964 A1 | 9/2019 | Oren |
| 2019/0304584 A1 | 10/2019 | Savolainen |
| 2019/0307983 A1 | 10/2019 | Goldman |
| 2019/0354632 A1 | 11/2019 | Mital et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0051446 A1 | 2/2020 | Rubinstein et al. |
| 2020/0066390 A1 | 2/2020 | Svendrys et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0334972 A1 | 10/2020 | Gopalakrishnan |
| 2020/0357299 A1 | 11/2020 | Patel et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |

(56) References Cited

U.S. PATENT DOCUMENTS

| | | | |
|---|---|---|---|
| 2021/0134456 | A1 | 5/2021 | Posnack et al. |
| 2021/0134457 | A1 | 5/2021 | Mason et al. |
| 2021/0134458 | A1 | 5/2021 | Mason et al. |
| 2021/0134463 | A1 | 5/2021 | Mason et al. |
| 2021/0138304 | A1 | 5/2021 | Mason et al. |
| 2021/0142875 | A1 | 5/2021 | Mason et al. |
| 2021/0142893 | A1 | 5/2021 | Guaneri et al. |
| 2021/0142898 | A1 | 5/2021 | Mason et al. |
| 2021/0142903 | A1 | 5/2021 | Mason et al. |
| 2021/0144074 | A1 | 5/2021 | Guaneri et al. |
| 2021/0186419 | A1 | 6/2021 | Van Ee et al. |
| 2021/0202090 | A1 | 7/2021 | ODonovan et al. |
| 2021/0202103 | A1 | 7/2021 | Bostic et al. |
| 2021/0244998 | A1 | 8/2021 | Hacking et al. |
| 2021/0345879 | A1 | 11/2021 | Mason et al. |
| 2021/0345975 | A1 | 11/2021 | Mason et al. |
| 2021/0350888 | A1 | 11/2021 | Guaneri et al. |
| 2021/0350898 | A1 | 11/2021 | Mason et al. |
| 2021/0350899 | A1 | 11/2021 | Mason et al. |
| 2021/0350901 | A1 | 11/2021 | Mason et al. |
| 2021/0350914 | A1 | 11/2021 | Guaneri et al. |
| 2021/0350926 | A1 | 11/2021 | Mason et al. |
| 2021/0366587 | A1 | 11/2021 | Mason et al. |
| 2021/0383909 | A1 | 12/2021 | Mason et al. |
| 2021/0391091 | A1 | 12/2021 | Mason |
| 2021/0407670 | A1 | 12/2021 | Mason et al. |
| 2021/0407681 | A1 | 12/2021 | Mason et al. |
| 2022/0015838 | A1 | 1/2022 | Posnack et al. |
| 2022/0028519 | A1 | 1/2022 | Mason et al. |
| 2022/0036988 | A1 | 2/2022 | Mason et al. |
| 2022/0036995 | A1 | 2/2022 | Mason et al. |
| 2022/0047921 | A1 | 2/2022 | Bissonnette et al. |
| 2022/0079690 | A1 | 3/2022 | Mason et al. |
| 2022/0080256 | A1 | 3/2022 | Arn et al. |
| 2022/0105384 | A1 | 4/2022 | Hacking et al. |
| 2022/0105385 | A1 | 4/2022 | Hacking et al. |
| 2022/0115133 | A1 | 4/2022 | Mason et al. |
| 2022/0126169 | A1 | 4/2022 | Mason |
| 2022/0148725 | A1 | 5/2022 | Mason et al. |
| 2022/0158916 | A1 | 5/2022 | Mason et al. |
| 2022/0193491 | A1 | 6/2022 | Mason et al. |

FOREIGN PATENT DOCUMENTS

| | | |
|---|---|---|
| CN | 202220794 U | 5/2012 |
| CN | 103488880 A | 1/2014 |
| CN | 104335211 A | 2/2015 |
| CN | 105620643 A | 6/2016 |
| CN | 105894088 A | 8/2016 |
| CN | 105930668 A | 9/2016 |
| CN | 106127646 A | 11/2016 |
| CN | 106510985 A | 3/2017 |
| CN | 107430641 A | 12/2017 |
| CN | 107736982 A | 2/2018 |
| CN | 108078737 A | 5/2018 |
| CN | 208573971 U | 3/2019 |
| CN | 112603295 A | 4/2021 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 C2 | 12/1996 |
| DE | 29620008 U1 | 2/1997 |
| DE | 19947926 A3 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 634319 B1 | 10/1999 |
| EP | 1034817 A1 | 9/2000 |
| EP | 2564904 A1 | 3/2013 |
| EP | 3264303 A1 | 1/2018 |
| EP | 3323473 A1 | 5/2018 |
| EP | 3688537 A1 | 8/2020 |
| EP | 3731733 A1 | 11/2020 |
| FR | 2527541 A2 | 12/1983 |
| GB | 141664 A | 11/1920 |
| GB | 2336140 A | 10/1999 |
| GB | 2372459 A | 8/2002 |
| GN | 107736982 A | 2/2018 |
| JP | 2003225875 A | 8/2003 |
| JP | 3198173 U | 6/2015 |
| JP | 6659831 B2 | 10/2017 |
| JP | 2019134909 A | 8/2019 |
| JP | 6573739 B1 | 9/2019 |
| JP | 6710357 B1 | 6/2020 |
| JP | 6775757 B1 | 10/2020 |
| JP | 2021026768 A | 2/2021 |
| JP | 2021027917 A | 2/2021 |
| KR | 20020009724 A | 2/2002 |
| KR | 20020065253 A | 8/2002 |
| KR | 20160093990 A | 8/2016 |
| KR | 20170038837 A | 4/2017 |
| KR | 20190056116 A | 5/2019 |
| KR | 101988167 B1 | 6/2019 |
| KR | 102116664 B1 | 7/2019 |
| KR | 102116968 B1 | 3/2020 |
| KR | 20200025290 A | 3/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102264498 B1 | 6/2021 |
| TW | 442956 B | 7/2014 |
| WO | 1998009687 A | 3/1998 |
| WO | 0149235 A2 | 7/2001 |
| WO | 2001050387 A1 | 7/2001 |
| WO | 2003043494 A1 | 5/2003 |
| WO | 2006004430 A2 | 1/2006 |
| WO | 2006012694 A1 | 2/2006 |
| WO | 2008114291 A1 | 9/2008 |
| WO | 2014178077 A2 | 11/2014 |
| WO | 2016154318 A1 | 9/2016 |
| WO | 2018171853 A1 | 9/2018 |
| WO | 2019022706 A1 | 1/2019 |
| WO | 2019204876 A1 | 4/2019 |
| WO | 2019083450 A1 | 5/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |

OTHER PUBLICATIONS

Claris Healthcare Inc.; Claris Reflex Patient Rehabilitation System Brochure, https://clarisreflex.com/, retrieved from internet on Oct. 2, 2019; 5 pages.
International Searching Authority, Search Report and Written Opinion for PCT/US2020/021876, dated May 28, 2020; 7 pages.

(56) References Cited

OTHER PUBLICATIONS

Fysiomed, "16983—Vario adjustable pedal arms", <https://www.fysiomed.com/en/products/16983-vario-adjustable-pedal-arms>, pulled from webpage on Aug. 4, 2020; 1 page.

Matrix, "R3xm Recumbent Cycle", <https://www.matrixfitness.com/en/cardio/cycles/r3xm-recumbent>, pulled from webpage on Aug. 4, 2020; 1 page.

Stephen R. Crow, Authorized Officer, PCT Notification of Transmittal of International Preliminary Report on Patentability, dated Dec. 11, 2018, PCT/US2017/50895, Alexandria, Virginia USA; 52 pages.

PCT International Search Report and Written Opinion, PCT/US17/50895 dated Jan. 12, 2018; 18 pages.

"ROMTech The Modem Techology of Rehabilitation" [retrieved Aug. 19, 2021]. Retrieved from the Internet: <https://https://www.romtech.com>.

HCI Fitness physio trainer, announced 2017 [online], [site visited Nov. 10, 2020], Available from internet, URL: https://www.amazon.com/HCI-Fitness-Physio Trainer-Electronically-Controlled/dp/B0759YMW78/ (Year: 2017).

"HCI Fitness physio trainer, announced 2009 [online], [site visited Nov. 10, 2020], Available from internet, URL: https://www.amazon.com/HCI-Fitness-PhysioTrainer-Upper-Ergonometer/dp/B001P5GUGM (Year: 2009)".

International Searching Authority, Search Report and Written Opinion for PCT/US20/56661, dated Feb. 12, 2021; 11 pages.

Dor-Haim, "A Novel Digital Platform for a Monitored Home-based Cardiac Rehabilitation Program". Journal of Visualized Experiments. Webpage <https://www.jove.com/video/59019>. Apr. 19, 2019; Entire Document.; 30 pages.

Kobsar, et al., 2018, "Wearable Sensor Data to Track Subject-Specific Movement Patterns Related to Clinical Dutcomes Using a Machine Learning Approach"; 12 pages.

International Searching Authority, Search Report and Written Opinion for International Application No. PCT/US2021/032807, dated Sep. 6, 2021, 11 pages.

Jennifer Bresnick, "What is the Role of Natural Language Processing in Healthcare?", pp. 1-7, published Aug. 18, 2016, retrieved on Feb. 1, 2022 from https://healthitanalytics.com/featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Davenport et al., "The Potential For Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods In Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

* cited by examiner

US 11,410,768 B2

METHOD AND SYSTEM FOR IMPLEMENTING DYNAMIC TREATMENT ENVIRONMENTS BASED ON PATIENT INFORMATION

CROSS-REFERENCE TO RELATED APPLICATIONS

This application is a continuation of U.S. patent application Ser. No. 17/147,232, filed Jan. 12, 2021, titled "Method and System for Implementing Dynamic Treatment Environments Based on Patient Information," which is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes.

BACKGROUND

Remote medical assistance, also referred to, inter alia, as remote medicine, telemedicine, telemed, telmed, tel-med, or telehealth, is an at least two-way communication between a healthcare provider or providers, such as a physician or a physical therapist, and a patient using audio and/or audio-visual and/or other sensorial or perceptive (e.g., without limitation, gesture recognition, gesture control, touchless user interfaces (TUIs), kinetic user interfaces (KUIs), tangible user interfaces, wired gloves, depth-aware cameras, stereo cameras, and gesture-based controllers, tactile, gustatory, haptic, pressure-sensing-based or electromagnetic (e.g., neurostimulation) communications (e.g., via a computer, a smartphone, or a tablet). Telemedicine may aid a patient in performing various aspects of a rehabilitation regimen for a body part. The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Telemedicine is an option for healthcare providers to communicate with patients and provide patient care when the patients do not want to or cannot easily go to the healthcare providers' offices. Telemedicine, however, has substantive limitations as the healthcare providers cannot conduct physical examinations of the patients. Rather, the healthcare providers must rely on verbal communication and/or limited remote observation of the patients.

SUMMARY

In one embodiment, a system that comprises a memory device storing instructions, and a processing device communicatively coupled to the memory device. The processing device executes the instructions to: receive user data obtained from records associated with a user; generate a modified treatment plan based on the user data; and send, to a treatment apparatus accessible to the user, the modified treatment plan, wherein the modified treatment plan causes the treatment apparatus to update at least one operational aspect of the treatment apparatus, and update at least one operational aspect of at least one other device communicatively coupled to the treatment apparatus.

In one embodiment, a method includes receiving user data obtained from electronic or physical records associated with a user. The method includes generating a modified treatment plan based on the user data. The method further includes sending, to a treatment apparatus accessible to the user, the modified treatment plan, wherein the modified treatment plan causes the treatment apparatus to: update at least one operational aspect of the treatment apparatus, and update at least one operational aspect of at least one other device communicatively coupled to the treatment apparatus.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which.

NOTATION AND NOMENCLATURE

Figure 1:
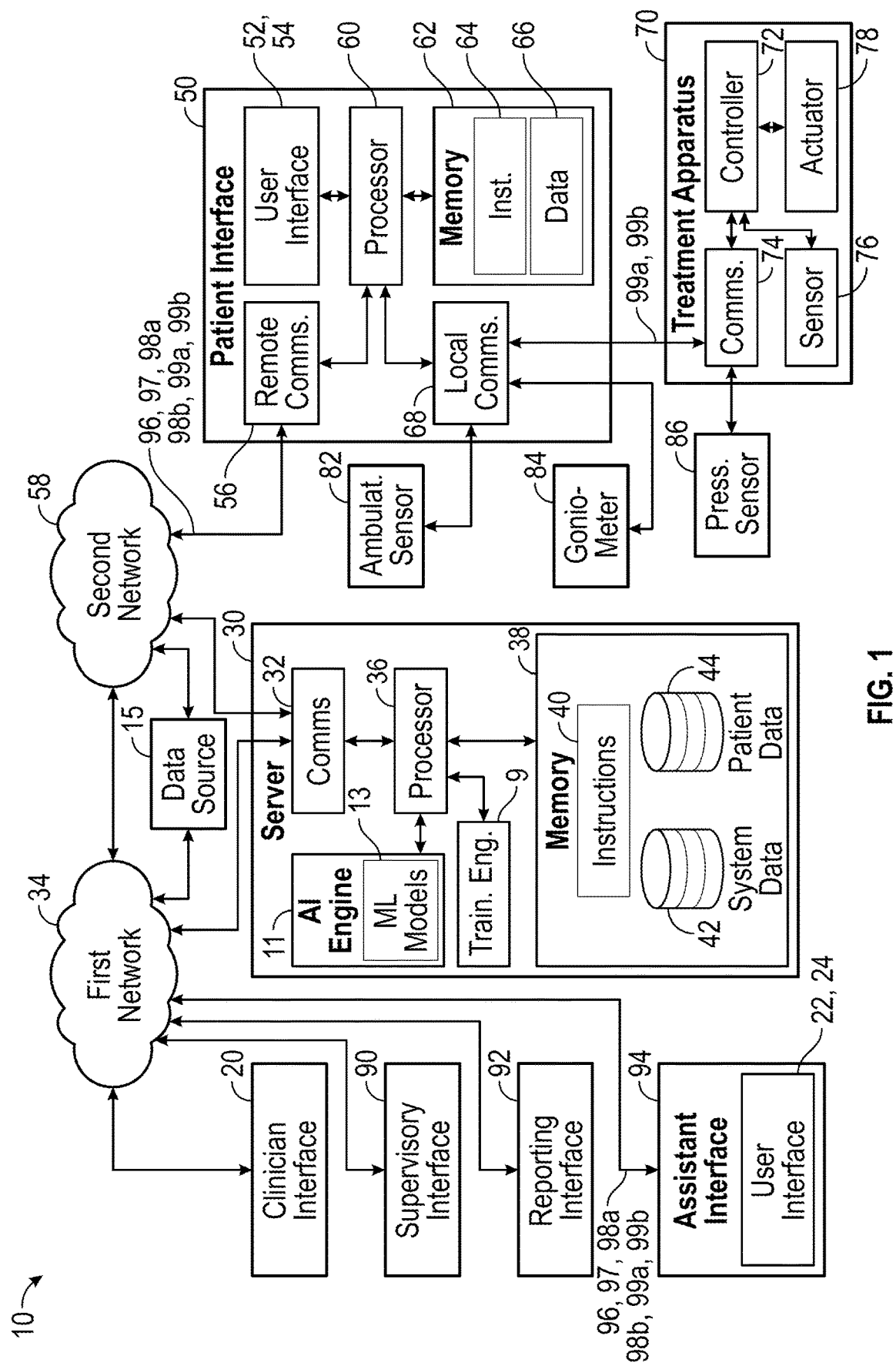
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, etc. may be used interchangeably herein.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; etiologic; cohort-associative; differentially diagnostic; surgical, physically therapeutic, pharmacologic, and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other medical professional may prescribe a treatment apparatus to the patient to use to perform a treatment protocol at their residence or any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

Since the physical therapist or other medical professional is located in a different location from the patient and the treatment apparatus, it may be technically challenging for the physical therapist or other medical professional to monitor the patient's actual progress (as opposed to relying on the patient's word about their progress) using the treatment apparatus, modify the treatment plan according to the patient's progress, adapt the treatment apparatus to the personal characteristics of the patient as the patient performs the treatment plan, and the like.

Accordingly, some embodiments of the present disclosure pertain to using artificial intelligence and/or machine learning to assign patients to cohorts and to dynamically control a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, or any suitable location, including permanent or temporary domiciles. In some embodiments, the treatment apparatuses may be communicatively coupled to a server. Characteristics of the patients may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan led to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the characteristics of the patients, the treatment plans performed by the patients, and the results of the treatment plans.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their characteristics is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may also be trained to output treatment plans that are not optimal or sub-optimal or even inappropriate (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient.

In some embodiments, the treatment plans and/or excluded treatment plans may be presented, during a telemedicine or telehealth session, to a medical professional. The medical professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text, and other multimedia information. Real-time may refer to less than or equal to 2 seconds. Near real-time may refer to any interaction of a sufficiently short time to enable two individuals to engage in a dialogue via such user interface and will generally be less than 10 seconds but greater than 2 seconds.

Presenting the treatment plans generated by the artificial intelligence engine concurrently with a presentation of the patient video may provide an enhanced user interface because the medical professional may continue to visually and/or otherwise communicate with the patient while also reviewing the treatment plans on the same user interface. The enhanced user interface may improve the medical professional's experience using the computing device and may encourage the medical professional to reuse the user interface. Such a technique may also reduce computing resources (e.g., processing, memory, network) because the medical professional does not have to switch to another user interface screen to enter a query for a treatment plan to recommend based on the characteristics of the patient. The artificial intelligence engine provides, dynamically on the fly, the treatment plans and excluded treatment plans.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a medical professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

According to some embodiments, all or a portion of the data described throughout this disclosure can be stored on/provided by a data source 15 with which the server 30 is communicably coupled. Moreover, the data source 15 can store patient data that can be retrieved and utilized by the server 30. For example, the data source 15 can provide access to data obtained from electronic medical records systems, insurance provider systems, and the like.

In addition, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices over time and stored in the database 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment apparatus 70, among other things. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of the characteristics of the people that used the treatment apparatus 70 to perform treatment plans, the details (e.g., treatment protocol including exercises, amount of time to perform the exercises, how often to perform the exercises, a schedule of exercises, parameters/configurations/settings of the treatment apparatus 70 throughout each step of the treatment plan, etc.) of the treatment plans performed by the people using the treatment apparatus 70, and the results of the treatment plans performed by the people. The one or more machine learning models 13 may be trained to match patterns of characteristics of a patient with characteristics of other people in assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, the machine learning apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output and generate the machine learning models 13 that capture these patterns. In some embodiments, the artificial intelligence engine 11, the system data store 42/patient data store 44, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spinwheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to assist or guide a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively, or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively, or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally, or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively, or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
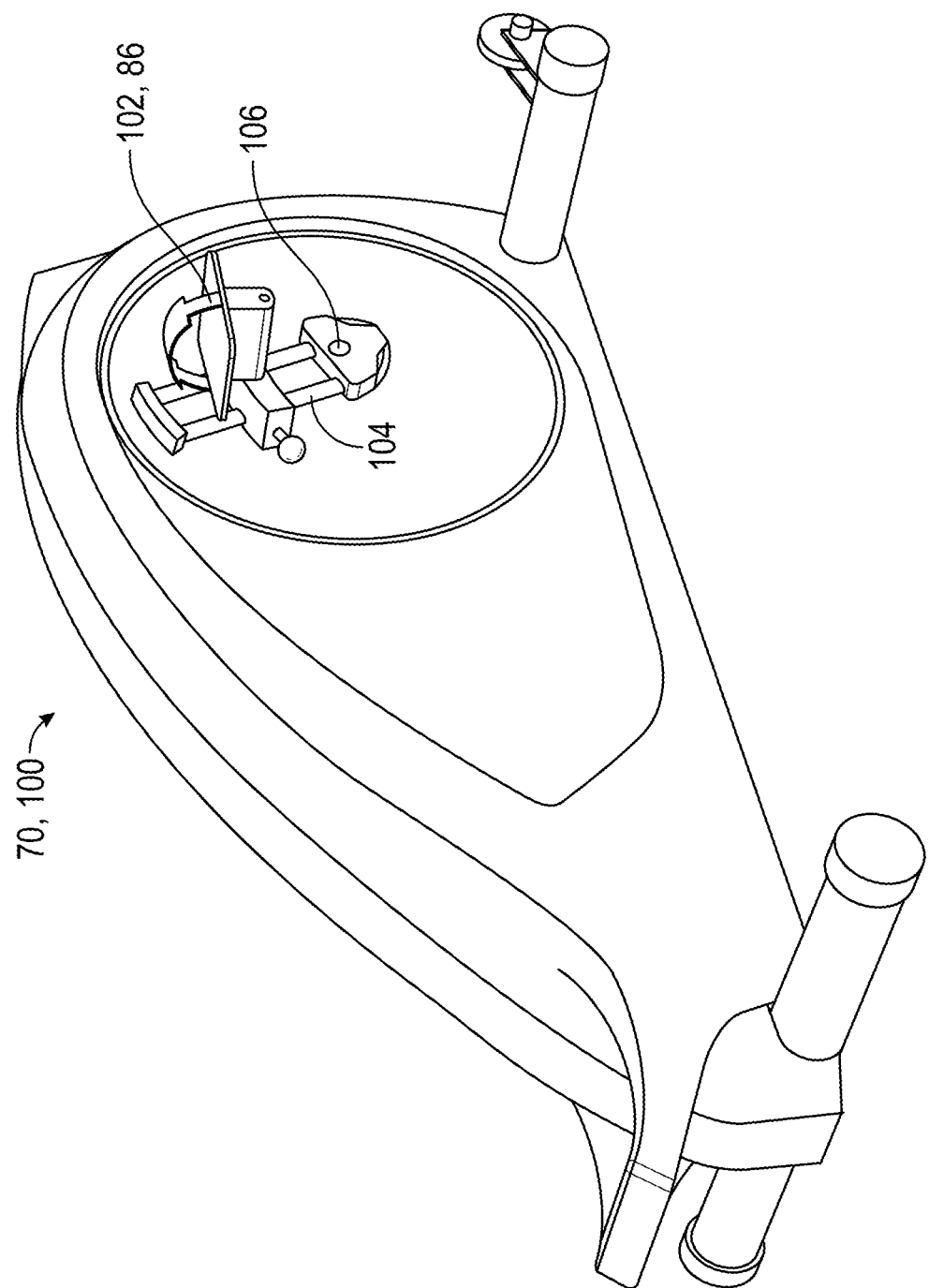
FIG. 2 shows a perspective view of an embodiment of a treatment apparatus according to the present disclosure.
Figure 3:
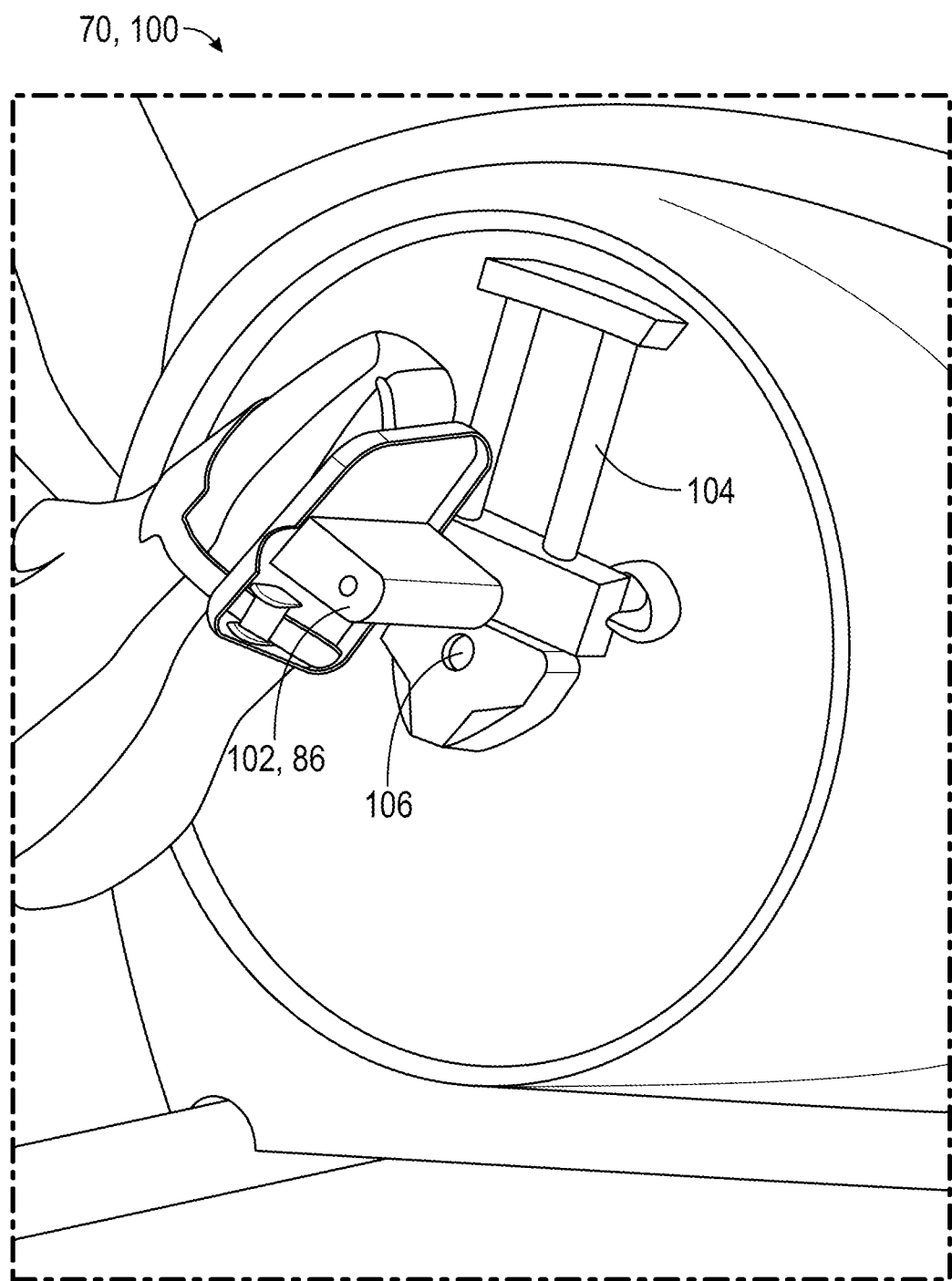
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
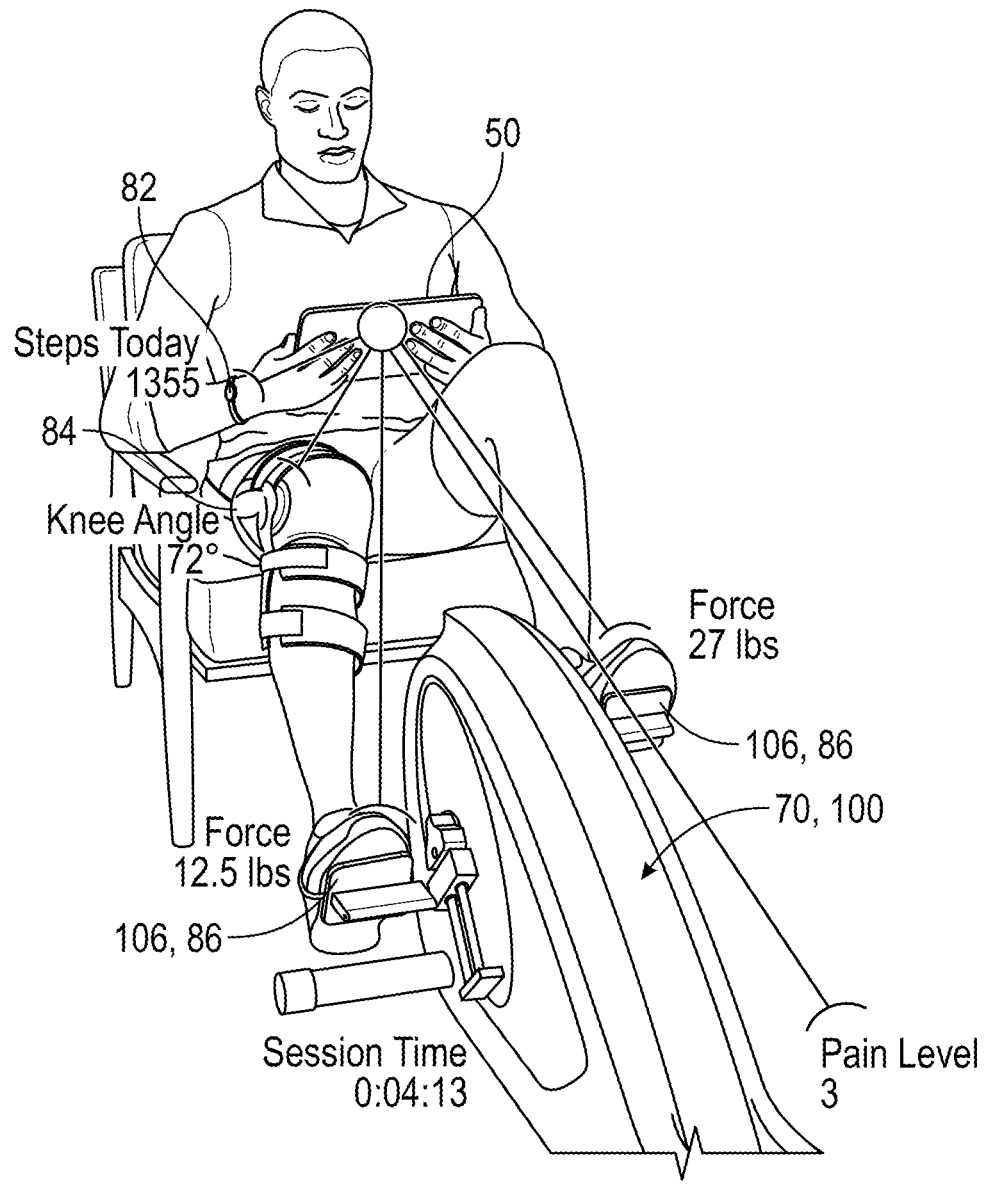
FIG. 4 shows a perspective view of a person using the treatment apparatus of FIG. 2 according to the present disclosure.

FIG. 4 shows a person (a patient) using the treatment apparatus of FIG. 2 and shows sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
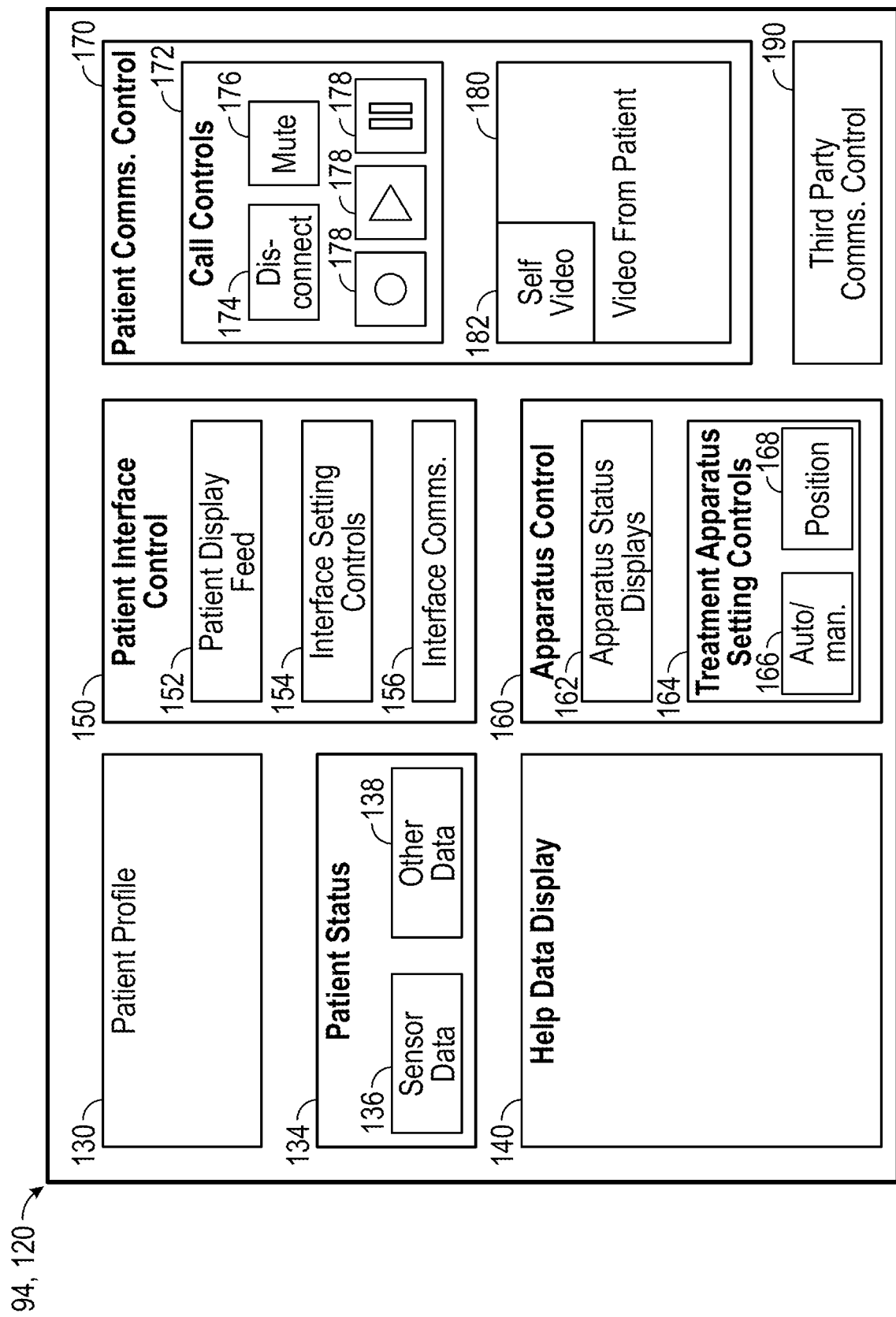
FIG. 5 shows an example embodiment of an overview display of an assistant interface according to the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a medical professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a medical professional, such as a doctor or physical therapist. For example, a medical professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant, for example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively, or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively, or additionally, the self-video display 182 may be presented separately and/or independently from the video feed display 180.

The example overview display 120 shown in FIG. 5 also includes a third-party communications control 190 for use in conducting audio and/or audiovisual communications with a third party. The third-party communications control 190 may take the form of a portion or region of the overview display 120, as shown in FIG. 5. The third-party communications control 190 may take other forms, such as a display on a separate screen or a popup window. The third-party communications control 190 may include one or more controls, such as a contact list and/or buttons or controls to contact a third-party regarding use of a particular piece of hardware or software, e.g., a subject matter expert, such as a medical professional or a specialist. The third-party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
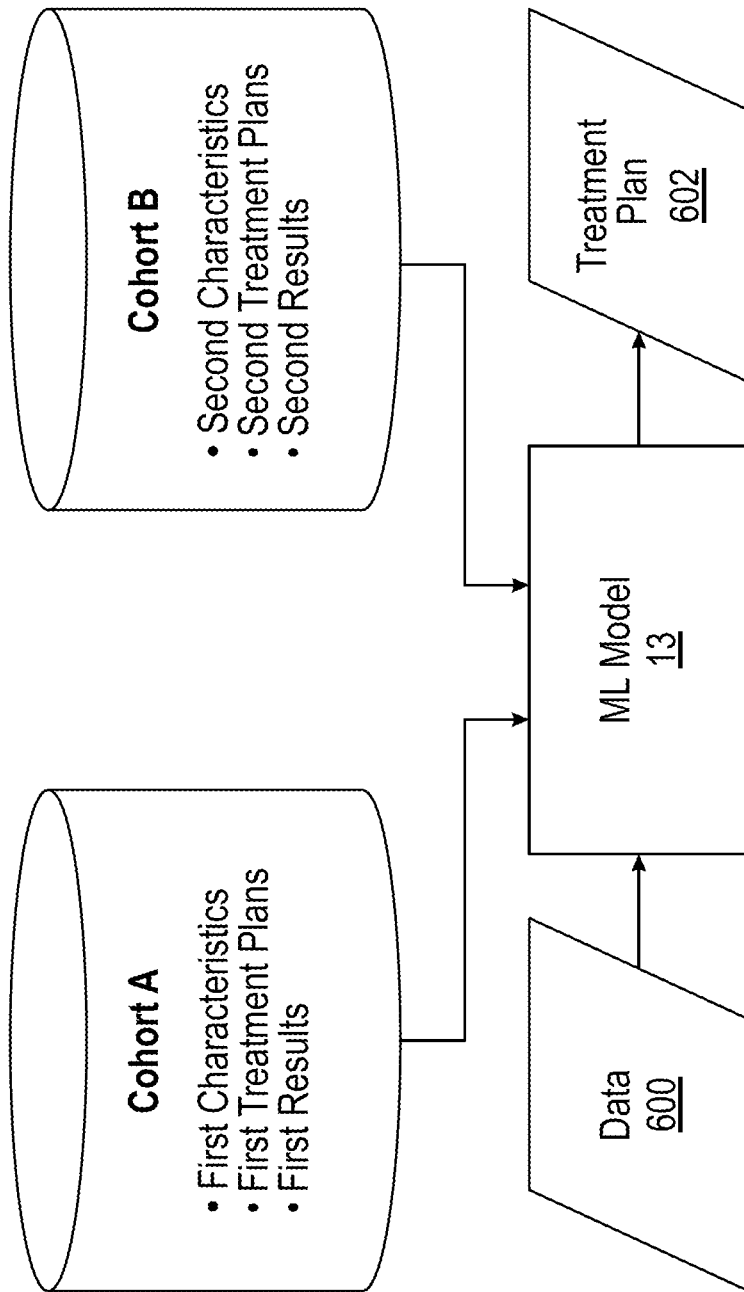
FIG. 6 shows an example block diagram of training a machine learning model to output, based on data pertaining to the patient, a treatment plan for the patient according to the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
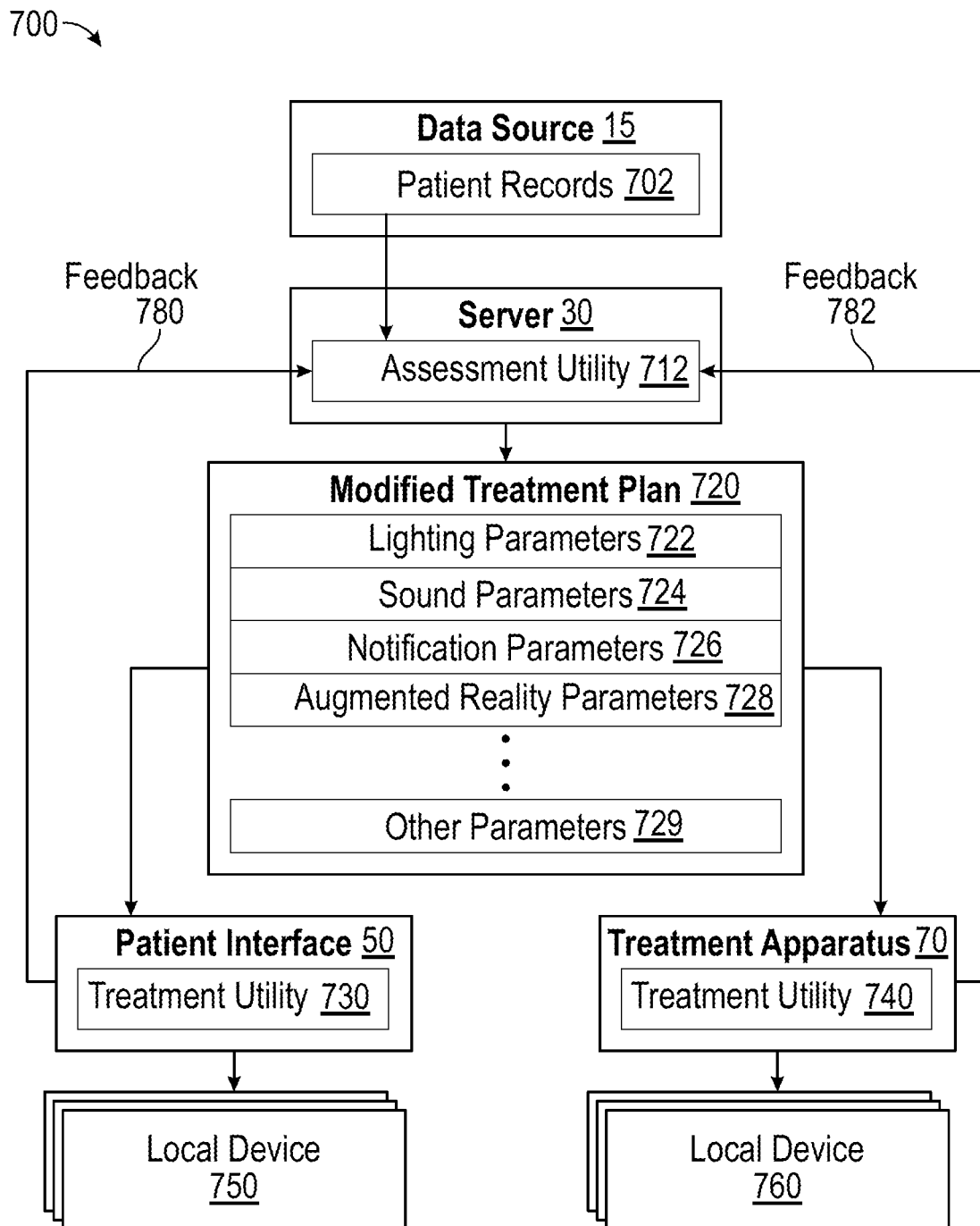
FIG. 7 illustrates a block diagram of a system for implementing dynamic treatment environments based on patient information, according to some embodiments.

FIG. 7 illustrates a block diagram of a system 700 for implementing dynamic treatment environments based on patient information, according to some embodiments. As shown in FIG. 7, the system 700 may include a data source 15, a server 30, a patient interface 50, a treatment apparatus 70, and local devices 750, 760. Notwithstanding the specific illustrations in FIG. 7, the number and/or organization of the various computing devices illustrated in FIG. 7 is not meant to be limiting. To the contrary, the system 700 may be adapted to omit and/or combine a subset of the devices illustrated in FIG. 7, or to include additional devices not illustrated in FIG. 7.

According to some embodiments, the data source 15 illustrated in FIG. 7 may represent the data source 15 illustrated in FIG. 1 or may represent any other data source(s) from which patient records may be obtained. In any case, the data source 15 may be configured to store information for various patients—e.g., the patient data 44 illustrated in FIG. 1—which is represented in FIG. 7 as patient records 702.

According to some embodiments, the patient records 702 may include, for each patient, occupational characteristics of the patient, health-related characteristics of the patient, demographic characteristics of the patient, psychographic characteristics of the patient, any other characteristics or attributes of the patient and the like.

According to some embodiments, the occupational characteristics for a given patient may include historical information about the patient's employment experiences, travel experiences, social interactions, and the like. For example, if a given patient is an active armed forces/military service member, then the employment experience information may include the patient's job roles, deployment history, rankings, and the like.

According to some embodiments, the health-related characteristics of the patent may include historical information about the patient's health, including a history of the patient's interactions with medical professionals, diagnoses received, prescriptions received, surgical procedures undertaken, past and/or ongoing medical conditions, dietary needs and/or habits, and the like. For example, the patient records 702 for a given patient may indicate that the patient has, e.g., ongoing endocrinological issues, where such issues affect the patient's overall psychological wellbeing.

According to some embodiments, the demographic characteristics for a given patient may include information pertaining to the age, sex, ethnicity, weight, height, etc., of the patient. For example, the patient records 702 for a given patient may indicate that the patient is a thirty-seven-year-old female of Asian descent.

Additionally, and according to some embodiments, the psychographic characteristics of the patient characteristics for a given patient may include information relating to the attitudes, interests, opinions, beliefs, activities, overt behaviors, motivating behaviors, etc., of the patient. For example, the patient records 702 for a given patient may indicate that the patient has suffered from social anxiety disorder for the past five years.

The foregoing types of patient records (occupational, health-related, demographic, psychographic, etc.) are merely exemplary and not meant to be limiting; further, any type of patient record—such as those previously herein—may be stored by the data source 15 consistent with the scope of this disclosure.

According to some embodiments, the server 30 illustrated in FIG. 7 may represent the server 30 illustrated in FIG. 1 or may represent another server device configured to implement the different techniques set forth herein. According to some embodiments, the server 30 may generate modified treatment plans 720 by using the various machine-learning functionalities described herein. For example, the server may utilize the AI engine 11, the ML models 13, the training engine 9, etc.—which are collectively represented in FIG. 7 as an assessment utility 712—to generate the modified treatment plans 720.

According to some embodiments, the assessment utility 712 may be configured to receive data pertaining to patients who have performed modified treatment plans 720 using different treatment apparatuses—e.g., the patient interface 50, the treatment apparatus 70, the local devices 750/760, and the like. In this regard, the data may include characteristics of the patients (e.g., patient records 702), the details of the modified treatment plans 720 performed by the patients, the results of performing the modified treatment plans 720, and the like. The results may include, for example, the feedback 780/782 received from the patient interface 50 and the treatment apparatus 70, feedback received from other devices (e.g., one or more of the clinician interface 20, the supervisory interface 90, the reporting interface 92, and the assistant interface 94), and the like. The foregoing feedback sources are not meant to be limiting; further, the assessment utility 712 may receive feedback from any conceivable source/individual consistent with the scope of this disclosure.

According to some embodiments, the feedback may include changes to the modified treatment plans 720 requested by the patients (e.g., in relation to performing the customized treatment plans 720), survey answers provided by the patients regarding their overall experience related to the customized treatment plans 720, information related to the patient's psychological and/or physical state during the treatment session (e.g., collected by sensors, by the patient, by a medical professional, etc.), and the like. A more detailed description of this feedback is described below in relation to FIGS. 8A-8H.

Accordingly, the assessment utility 712 may utilize the machine-learning techniques described herein to generate a modified treatment plan 720 for a given patient. According to some embodiments, and as shown in FIG. 7, a modified treatment plan 720 may include lighting parameters 722, sound parameters 724, notification parameters 726, augmented reality parameters 728, and other parameters 729. The foregoing parameters are exemplary and not meant to be limiting. The modified treatment plan 720 may include any information necessary to facilitate a treatment session as described herein, e.g., connectivity information, pre-recorded content, interactive content, overarching treatment plan information (associated with the modified treatment plan 720), and so on.

Further, as shown in FIG. 7, according to the modified treatment plan 720, the patient interface 50 and the treatment apparatus 70 may be configured to implement treatment utilities 730 and 740, respectively, to enable the patient interface 50 and the treatment apparatus 70 to self-configure. Although not illustrated in FIG. 7, one or more of the local devices 750/760 to which the patient interface 50 and the treatment apparatus 70 are communicatively coupled may implement respective treatment utilities that enable the local devices 750/760 to self-configure. This may not be required, however, in scenarios based on the modified treatment plan 720 in which one or more of the patient interface 50 and the treatment apparatus 70 possess the ability to adjust the configurations of one or more of the local devices 750/760.

According to some embodiments, the lighting parameters 722 may specify the manner in which one or more light sources should be configured in order to enhance the patient's overall experience. More specifically, the lighting parameters 722 may enable one or more devices on which the modified treatment plan 720 is being implemented—e.g., the patient interface 50, the treatment apparatus 70, the local devices 750/760, etc. (hereinafter, "the recipient devices")—to identify light sources, if any, that are relevant to (i.e., nearby) the user and are at least partially configurable according to the lighting parameters 722. The configurational aspects may include, for example, the overall brightness of a light source, the color tone of a light source, and the like. In one example, a patient may have installed one or more smart lights for light sources, e.g., Phillips Hue smart lights, Lutron Caséta smart lights, etc., in a room in which the patient typically conducts the treatment sessions, where the brightness, the color tone, etc. of the smart lights may be dynamically modified by commands. In another example, a patient may have installed one or more traditional lights (e.g., incandescent, light emitting diode (LED), etc.) linked to a controller that can affect the brightness, color tone, etc. output by the one or more traditional lights. In any case, the recipient device can be configured to adjust identified light sources in accordance with the lighting parameters 722.

According to some embodiments, the sound parameters 724 may specify the manner in which one or more sound sources may be configured to enhance the patient's overall experience. More specifically, the sound parameters 724 may enable one or more of the recipient devices to identify speakers (and/or amplifiers to which one or more speakers are connected), if any, wherein both are nearby the user and at least partially configurable according to the sound parameters 724. The configurational aspects may include, for example, an audio file and/or stream to play back, a volume at which to play back the audio file and/or stream, sound settings (e.g., bass, treble, balance, etc.), and the like. In one example, one of the recipient devices may be linked to one or more wired or wireless speakers, headphones, etc. located in a room in which the patient typically conducts the treatment sessions.

According to some embodiments, the notification parameters 726 may specify the manner in which one or more nearby computing devices may be configured to enhance the patient's overall experience. More specifically, the notification parameters 726 may enable one or more of the recipient devices to adjust their own (or other devices') notification settings. In one example, this may include updating configurations to suppress at least one of audible, visual, haptic, or physical alerts, to minimize distractions to the patient during the treatment session. This may also include updating a configuration to cause one or more of the recipient devices to transmit all electronic communications directly to an alternative target comprising one of voicemail, text, email, or other alternative electronic receiver.

According to some embodiments, the augmented reality parameters 728 may specify the manner in which one or more of the recipient devices are configured to provide an augmented reality experience to the patient. This may include, for example, updating a virtual background displayed on a display device communicatively coupled to one or more of the recipient devices. The techniques set forth herein are not limited to augmented reality but may also apply to virtual (or other) reality implementations. For example, the augmented reality parameters 728 may include information enabling a patient to participate in a treatment session using a virtual reality headset configured in accordance with one or more of the lighting parameters 722, sound parameters 724, notification parameters 726, augmented reality parameters 728, or other parameters 729. Further, any suitable immersive reality shall be deemed to be within the scope of the disclosure.

According to some embodiments, when a healthcare professional is conducting the treatment session, the other parameters 729 may represent any other conceivable parameters that may be used to adjust the patient's environment. The other parameters 729 may include, for example, configuration parameters for exercise equipment, which are described below in greater detail in relation to FIGS. 8G-8H.

Additionally, based on the parameters included in the modified treatment plan 720, one or more of the recipient devices may take snapshots of their own (or other devices') existing configurations prior to adjusting said devices. In this manner, the one or more recipient devices may restore the configurations at the conclusion of the treatment session, thereby improving the patient's overall experience.

The foregoing types of parameters (lighting, sound, notification, augmented reality, other, etc.) are merely exemplary and not meant to be limiting; further, any type of parameter—such as those previously herein—may be adjusted consistent with the scope of this disclosure.

Figure 8A:
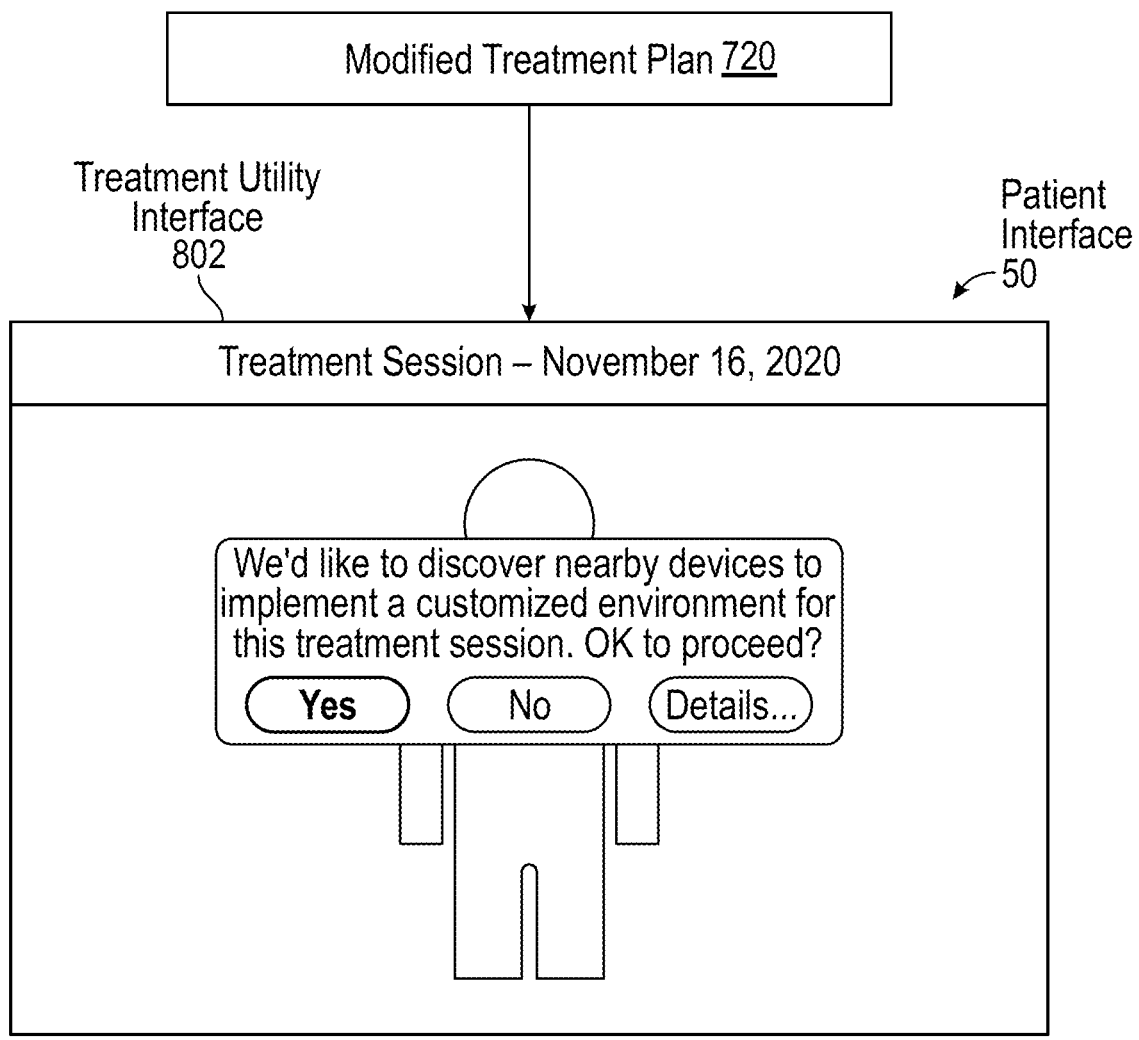
FIGS. 8A-8H illustrate conceptual diagrams for implementing a dynamic treatment environment based on a patient's information, according to some embodiments.

FIGS. 8A-8H illustrate conceptual diagrams for implementing a dynamic treatment environment based on a patient's information, according to some embodiments. In particular, FIG. 8A illustrates an example scenario in which the patient interface 50 receives a modified treatment plan 720—which, as described above, may be provided by the server 30 using the manual and/or automated (e.g., machine-learning) techniques described herein. According to some embodiments, the patient interface 50, in response to receiving the modified treatment plan 720, may output a treatment utility interface 802 (e.g., on a display communicably coupled to the patient interface 50). In the example illustrated in FIG. 8A, the patient interface 50 may seek to discover nearby devices in response to identifying that the modified treatment plan 720 includes parameters (e.g., lighting, sound, notification, etc.) intended to modify the configuration settings of nearby devices. As shown in FIG. 8A, a patient operating the patient interface 50 may authorize the discovery of nearby devices.

According to some embodiments, based on the parameters included in the modified treatment plan 720, the patient interface 50 may limit the discovery process. For example, when only lighting parameters 722 (and not the other parameters described herein) are included in the modified treatment plan 720, the patient interface 50 may search for light sources only. The patient interface 50 may also limit its discovery only to devices nearby the patient's known or likely location. For example, the patient interface 50 may reliably assume that devices coupled to the patient interface 50 via low-energy communications (e.g., Bluetooth, Near Field Communication, etc.) are nearby. In another example, the patient interface 50 may identify devices nearby based on names, tags, etc. assigned to the devices. For example, the patient interface 50 may prompt the patient to indicate the name of the room in which the patient is currently sitting (e.g., "Home Office"), and, in turn, discover nearby devices based on the name of the room. In yet another example, machine-learning techniques may be implemented to reliably predict the room in which the patient is located when the treatment session is about to begin. For example, the patient interface 50 may identify that, during virtually every prior treatment session, the patient was located in the "Home Office." In this manner, the patient interface 50 may automatically limit its search for devices in that room prior to starting each treatment session. Additionally, the patient interface 50 may be configured to forego the discovery process after identifying that the same devices are consistently utilized over a threshold number of treatment sessions.

Figure 8B:
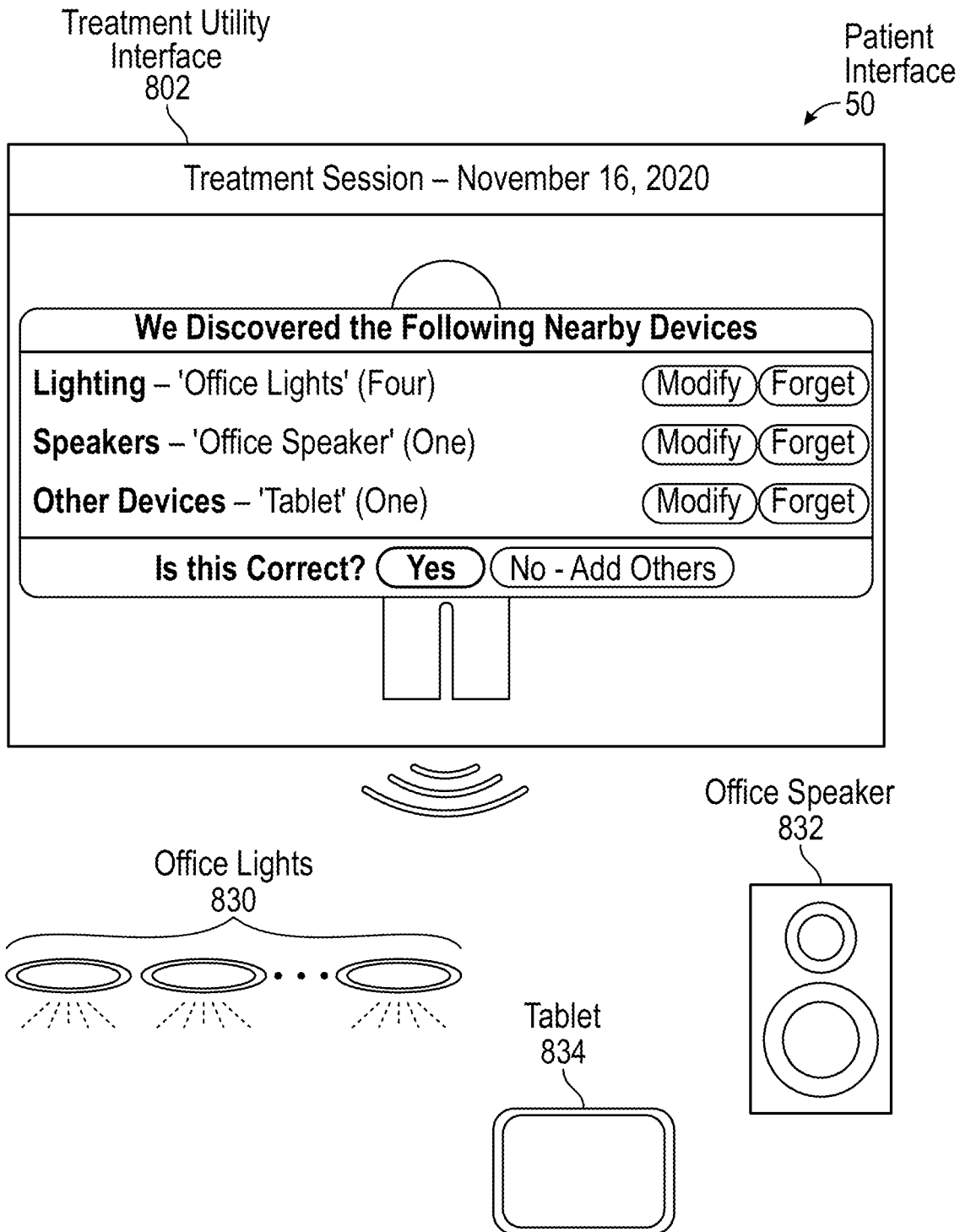

FIG. 8B illustrates an example outcome of the patient interface 50 presents nearby devices (as established in FIG. 8A) associated with the patient interface 50. As shown in FIG. 8B, the patient interface 50 indicates, by way of the treatment utility interface 802, that the patient interface 50 has discovered office lights 830 (four different light sources under the name "Office Lights"), an office speaker 832 (under the name "Office Speaker"), and a tablet 834 (under the name "Tablet").

According to other embodiments, the treatment utility interface 802 may enable the patient to add other devices not discovered by the patient interface 50 when performing the search. For example, adding other devices may involve enabling the patient to select from a list of devices filtered out during discovery (e.g., per the techniques described in the foregoing paragraph). Adding other devices may also involve enabling the patient to enter information necessary to discover and/or connect to other devices, such as device names, device addresses, device authentication information, and the like.

The foregoing discovery techniques are not meant to be limiting; further, any discovery technique, with any level of filtering, may be performed consistent with the scope of this disclosure.

Additionally, and as shown in FIG. 8B, the treatment utility interface 802 may enable the patient to modify the devices discovered by the patient interface 50. For example, the patient may select the respective "Modify" button located next to a given group of discovered devices to add, modify, or remove devices from the group. The treatment utility interface 802 may also enable the patient to instruct the patient interface 50 to forget one or more groups of devices, both in a temporary capacity (e.g., for the current session only) or in a more permanent capacity (e.g., until the patient removes the group from a list of forgotten devices). Such modifications may be communicated back to the server 30 in the form of feedback that may be used to improve the overall accuracy of the machine-learning techniques described herein.

As shown in FIG. 8B, the patient may verify the accuracy of the list of nearby devices presented in the treatment utility interface 802. In turn, the treatment utility interface 802 may indicate to the patient the recommended settings for the various devices when implementing the modified treatment plan 720, which is illustrated in FIG. 8C and described below in greater detail.

Figure 8C:
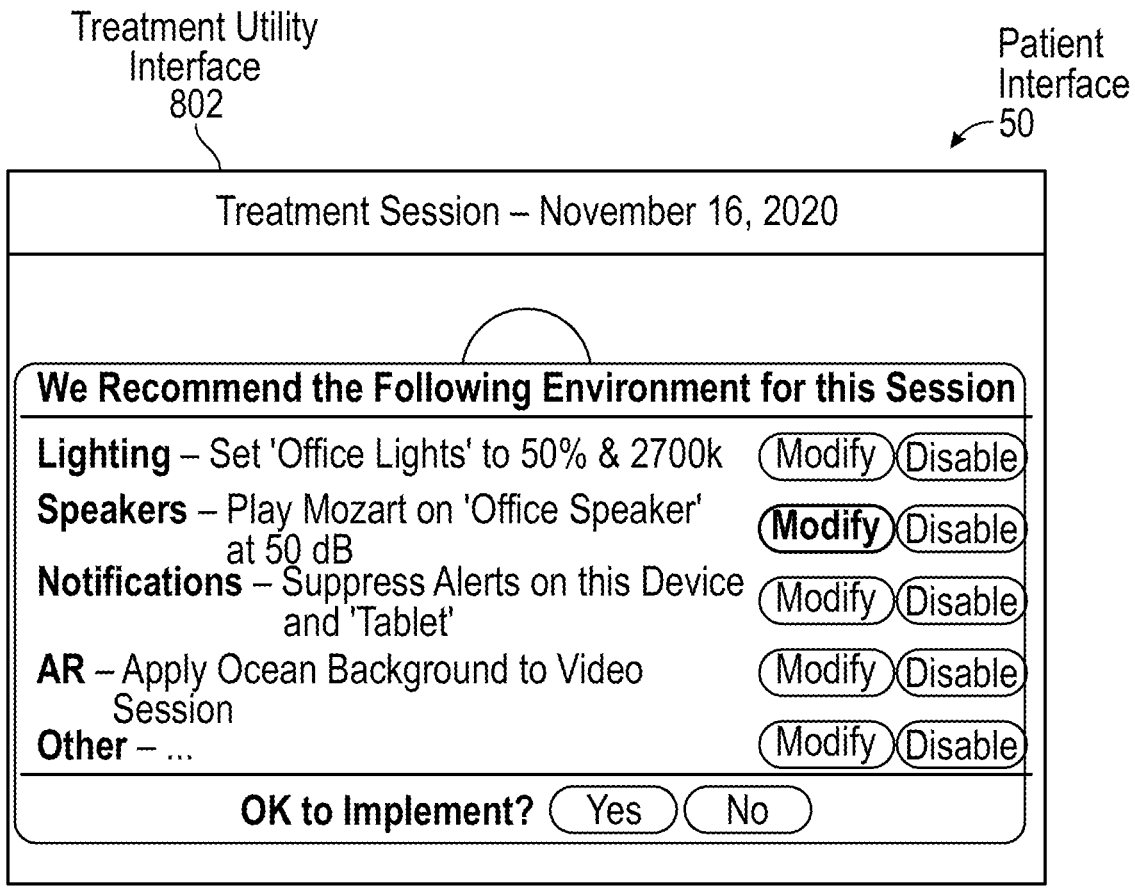
Figure 8C:
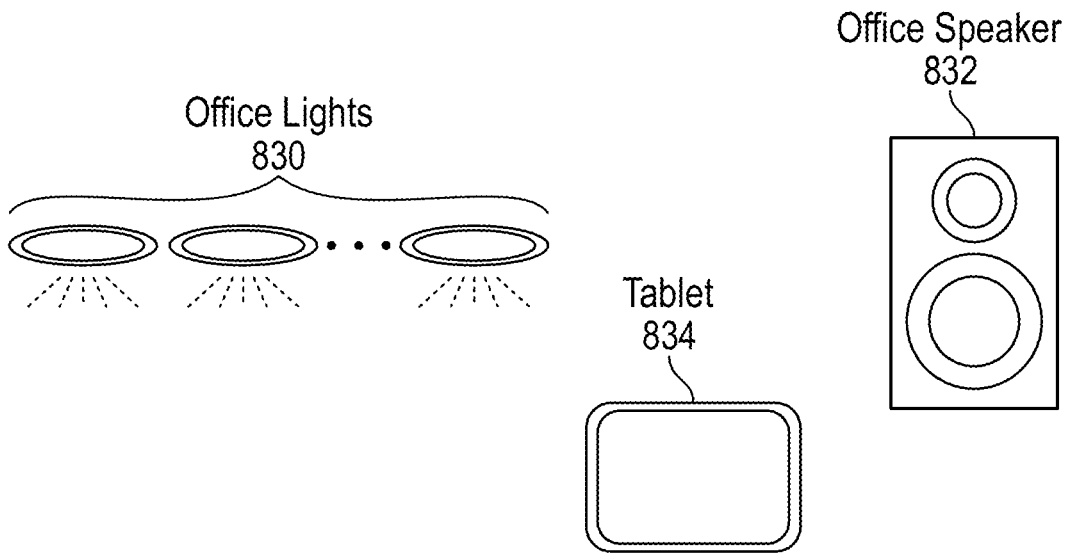

As shown in FIG. 8C, the various parameters included in the modified treatment plan 720 may be applied to the devices discovered (as established in FIGS. 8A-8B). For example, the lighting parameters 722 of the modified treatment plan 720 may involve setting the office lights 830 to a 50% brightness level and a color tone of 2700K. The sound parameters 724 of the modified treatment plan 720 may involve setting the office speaker 832 to play, e.g., a Mozart composition, at a volume level of 50 dB. Further, one or more audio files may be included in the sound parameters 724 to enable the office speaker 832 to play back audio designed to accompany the modified treatment plan 720. Alternatively, or additionally, instructions for obtaining audio data may be included in the sound parameters 724, e.g., a web address, credentials, etc. to stream audio designed to accompany the modified treatment plan 720.

In other embodiments, the notification parameters 726 of the modified treatment plan 720 may involve suppressing all alerts on the patient interface 50 and the tablet 834 such that, during the treatment session, the patient is not disturbed or distracted. Additionally, the augmented reality parameters 728 of the modified treatment plan 720 may involve applying a fixed/live ocean background to a video session that comprises the treatment session (e.g., wherein a clinician is superimposed over the live ocean background). This background may be visible, for example, on a display device communicatively coupled to the patient interface 50 (or other device with which the patient interface 50 is in communication). Additionally, the other parameters 729 of the modified treatment plan 720 may be used to apply any other additional settings to other recipient devices.

Additionally, as shown in FIG. 8C, the treatment utility interface 802 may enable the patient to disable or modify the suggested settings listed for the various devices. In the example illustrated in FIG. 8C, the patient opts to modify the suggested settings listed for the office speaker 832, which is described below in greater detail in relation to FIG. 8D. Such modifications may be applied in a temporary capacity (e.g., for the current session only) or in a more permanent capacity (e.g., until the patient indicates it is acceptable to utilize the respective device as suggested by the modified treatment plan 720). Moreover, such modifications may be communicated back to the server 30 in the form of feedback that may be used to improve the overall accuracy of the machine-learning techniques described herein.

Figure 8D:
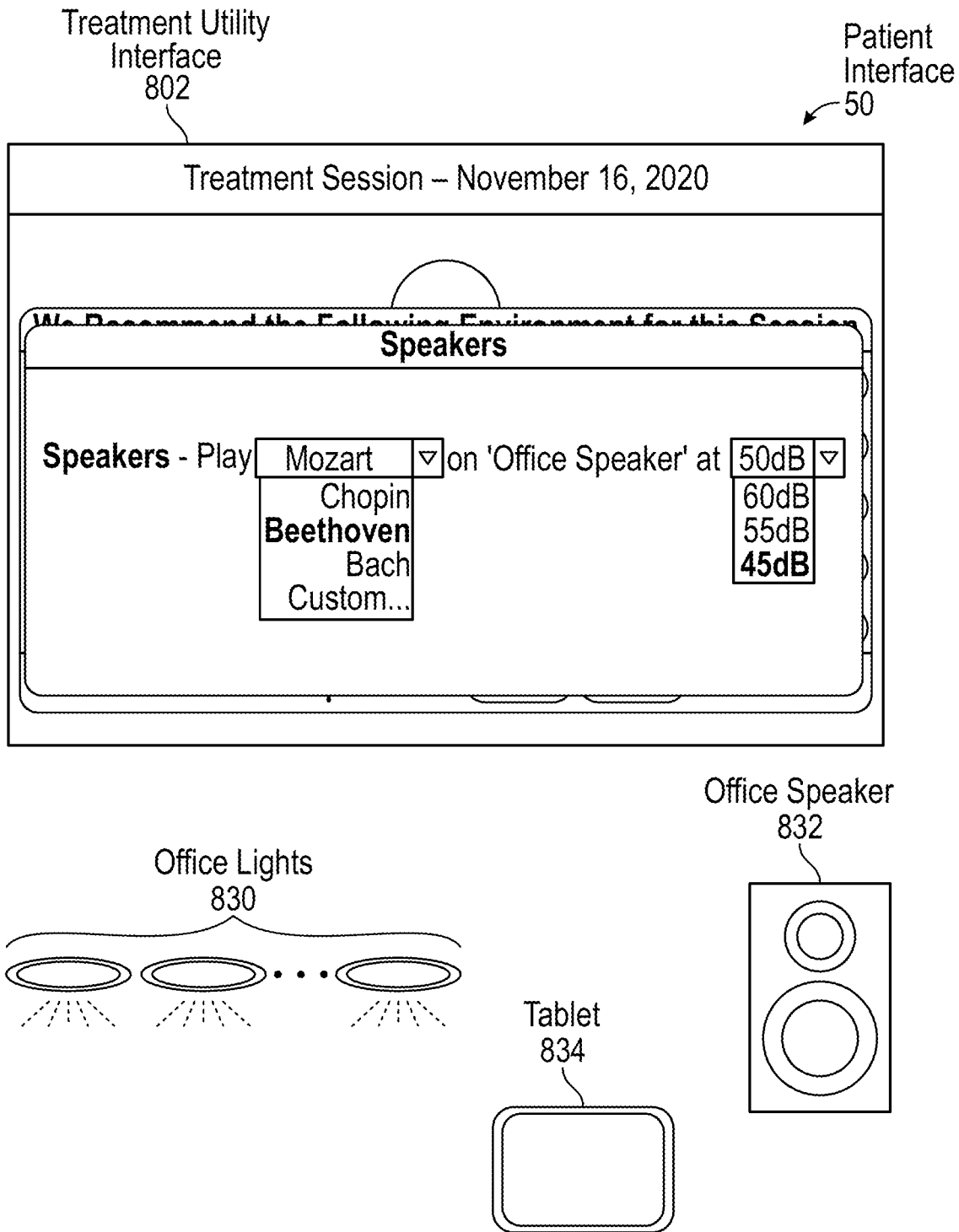

As shown in FIG. 8D, the treatment utility interface 802 may enable the patient to adjust the type and volume of the audio track that will be played back by the office speaker 832. For example, the patient may select alternative music (e.g., a Beethoven composition or, alternatively, e.g., a jazz, a pop, or a Reggae composition) if the patient does not like Mozart's music. The patient may also select a different volume at which to output the music, e.g., a lower or higher volume than the volume recommended by the modified treatment plan 720. The patient is not limited, however, to modifying the parameters illustrated in FIG. 8D. To the contrary, the treatment utility interface 802 may enable the patient to select other desired music from other desired sources (e.g., a local music library, streaming music services, etc.), to select from different playlists, and so on, consistent with the scope of this disclosure.

Figure 8E:
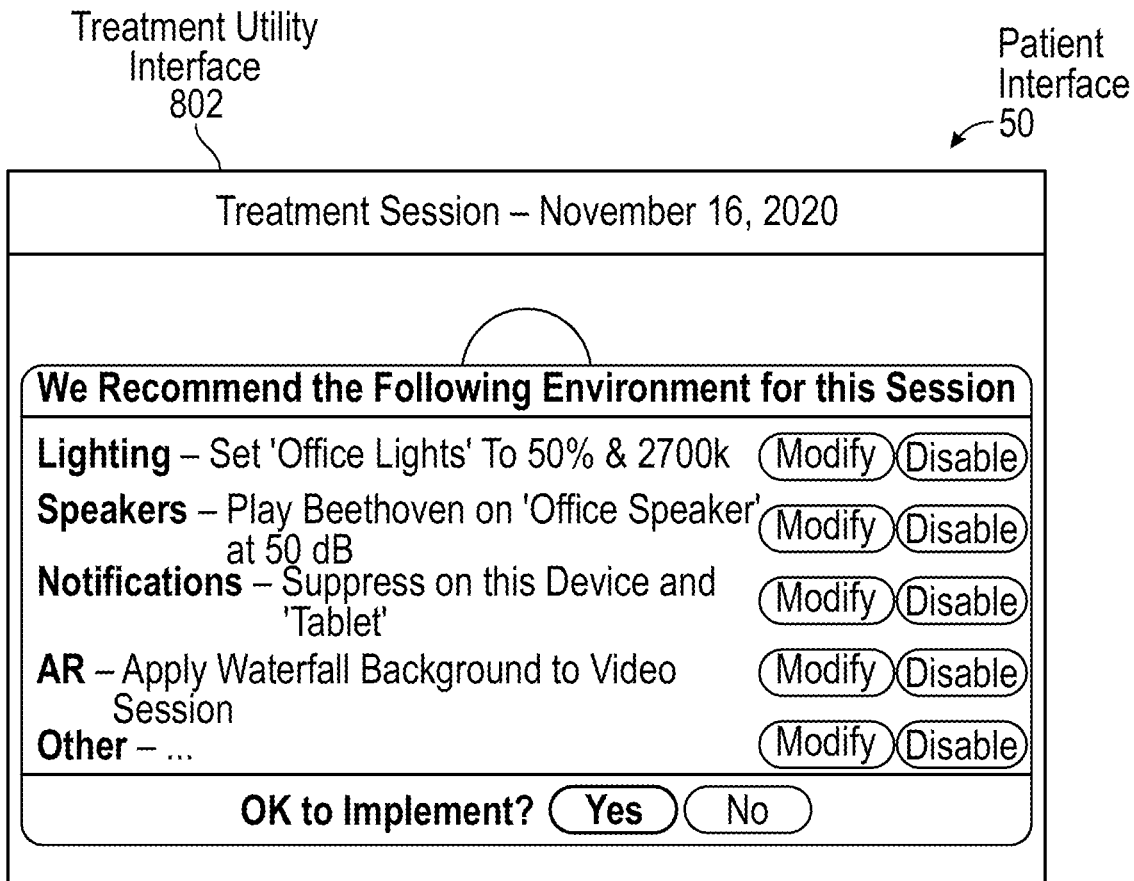
Figure 8E:
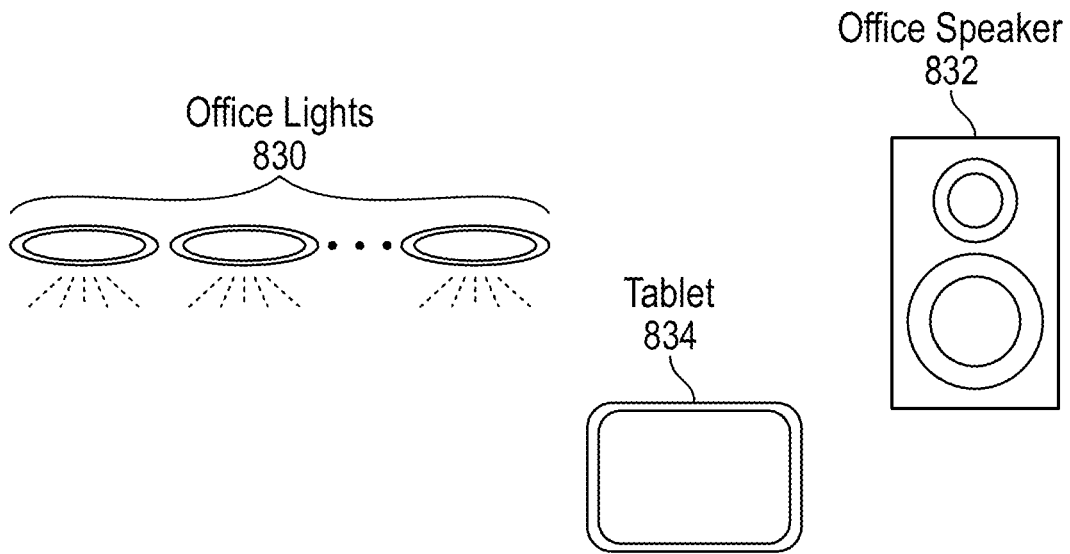

In the example illustrated in FIG. 8D, the patient modifies the sound parameters 724 by selecting a soundtrack of Beethoven compositions (instead of Mozart compositions) and selecting a volume of 45 dB (instead of 50 dB). FIG. 8E illustrates the treatment utility interface 802 after the patient has requested the changes (as established in FIG. 8D). At this juncture, the patient confirms that the recommended parameters are acceptable by selecting "YES". In turn, and as illustrated in FIG. 8F, the treatment utility interface 802 causes the different devices to reflect the settings illustrated in FIG. 8E.

Figure 8F:
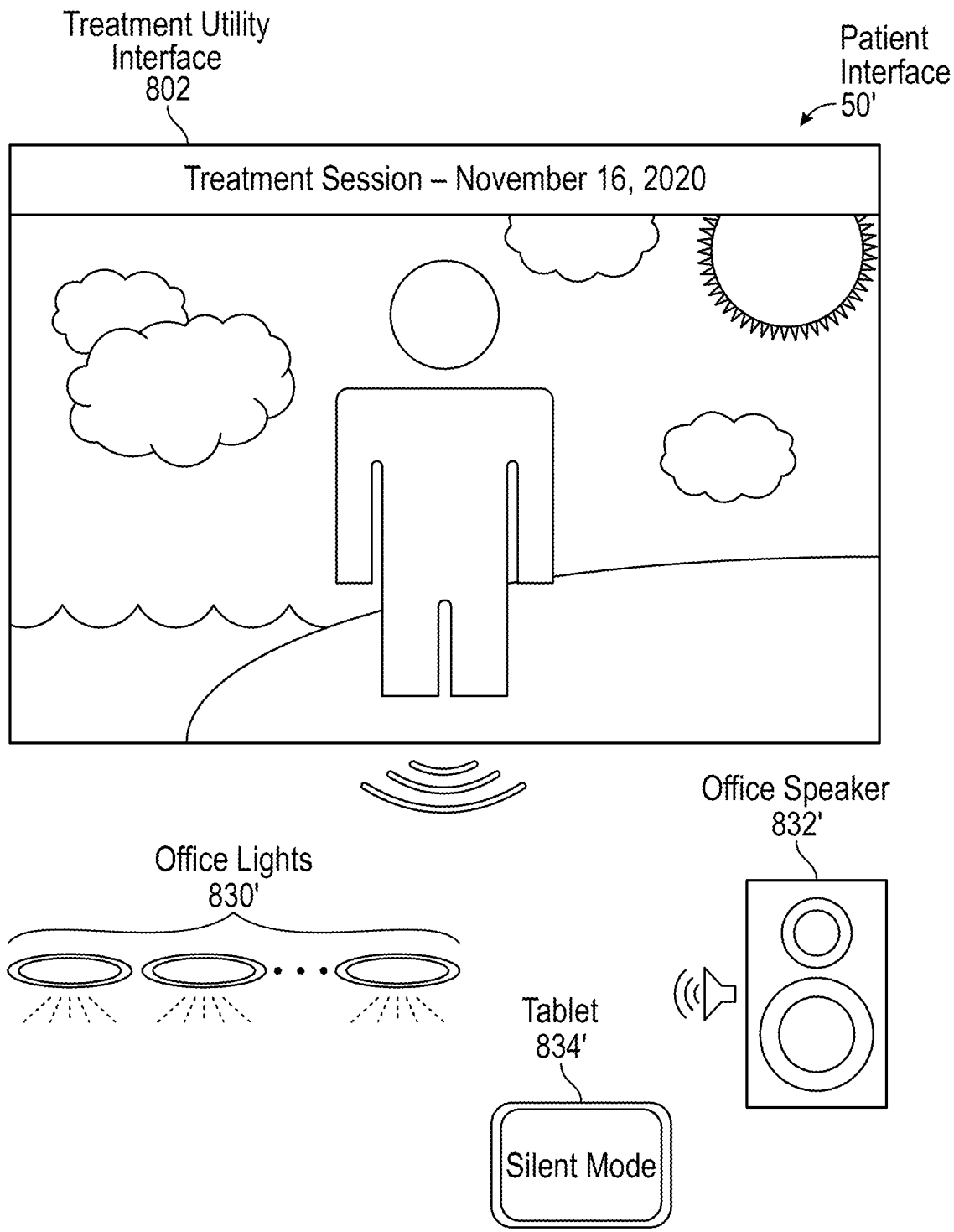

As shown in FIG. 8F, the office lights 830 (illustrated as the office lights 830' due to their adjusted settings) are configured to output light at a 50% brightness level and a 2700K color tone. The office speaker 832 (illustrated as the office speaker 832' due to its adjusted settings) begins playing a Beethoven composition at 45 dB. Additionally, the tablet 834 (illustrated as the tablet 834' due to its adjusted settings) has entered into a silent mode. Finally, the patient interface 50 (illustrated as the patient interface 50' due to its adjusted settings) has entered into a silent mode and is displaying a soothing live ocean background as an augmented reality. At this juncture, the training session may begin.

Figure 8G:
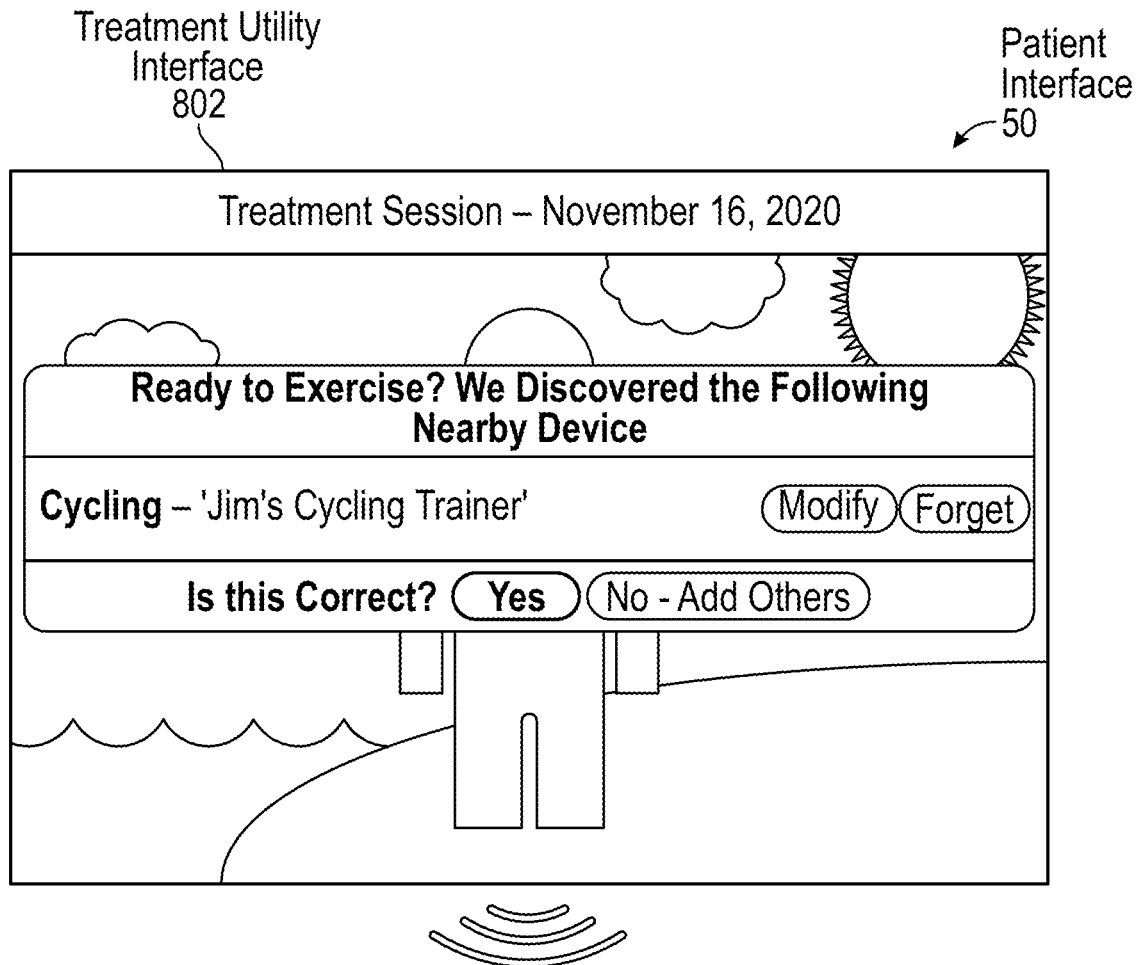
Figure 8G:
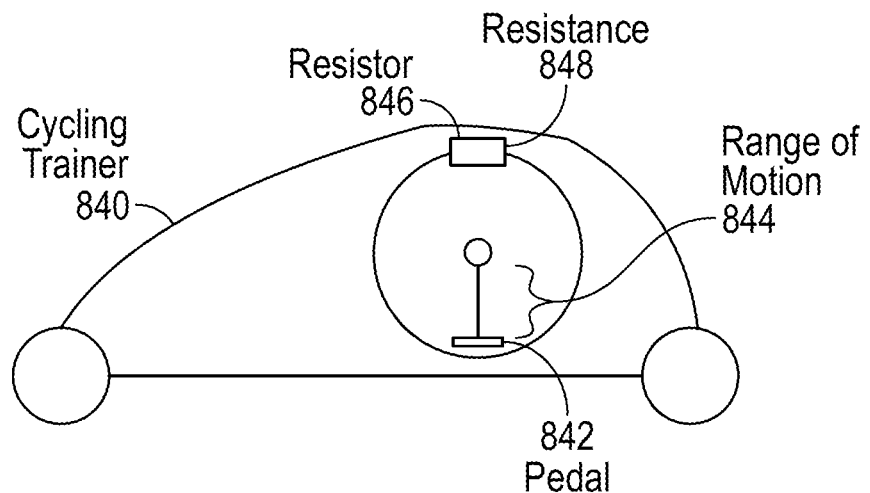

Additionally, FIG. 8G illustrates an example scenario involving the incorporation of an exercise session into a treatment session (e.g., as a continuation of the treatment session established in FIGS. 8A-8F, as a new/different treatment session, etc.). As shown in FIG. 8G, the exercise session may involve the patient interface 50 discovering nearby exercise devices. To identify the types of exercise devices compatible with the exercise session, this may involve, for example, referencing other parameters 729 included in the modified treatment plan 720. In the example illustrated in FIG. 8G, the patient interface 50 discovers a cycling trainer 840 named "Jim's Cycling Trainer" (based on, for example, the other parameters 729 of the modified treatment plan 720 indicating that cycling trainers are acceptable).

According to some embodiments, the cycling trainer 840 may represent the treatment apparatus 70 described in FIGS. 1-4 or may represent a different cycling trainer. As shown in FIG. 8G, the cycling trainer 840 may include one or more adjustable pedals 842 modifiable to establish a range of motion 844. The cycling trainer 840 may also include a resistor 846 modifiable to establish a resistance 848 against the rotational motion of the one or more pedals 842.

Figure 8H:
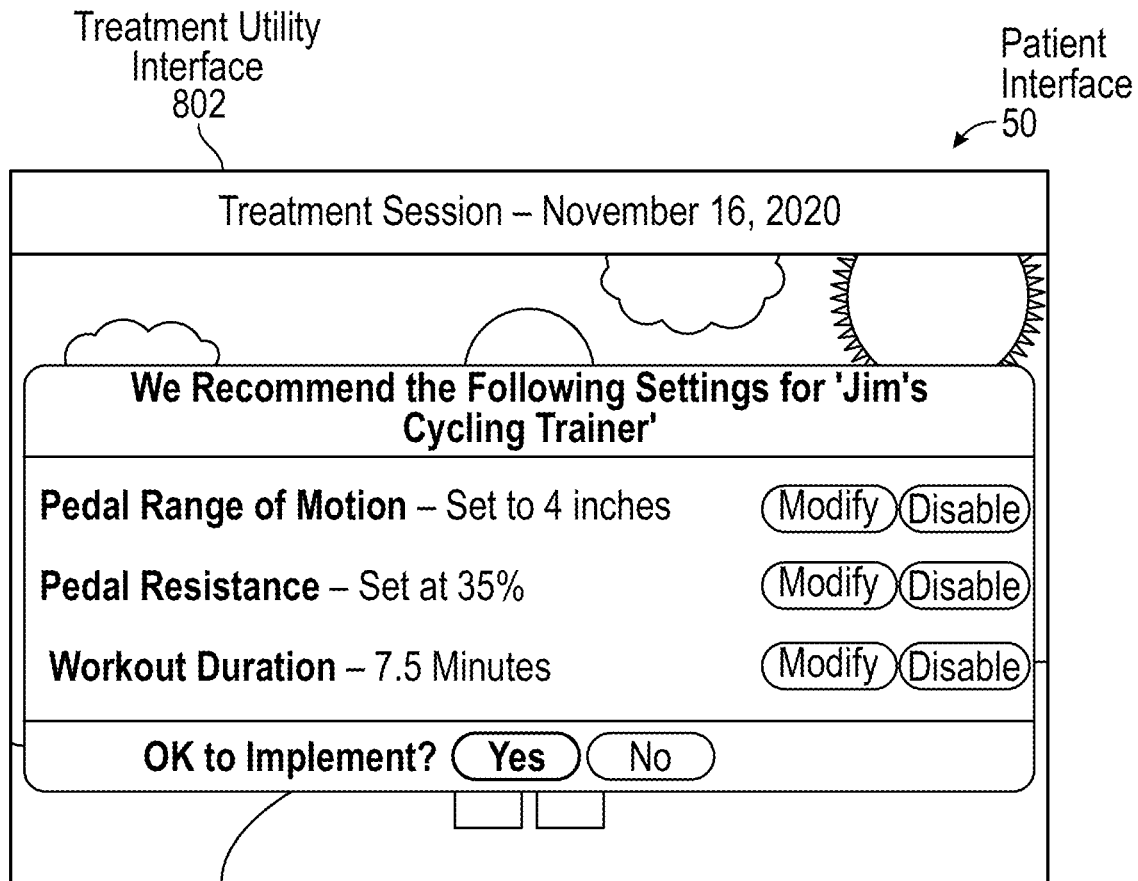
Figure 8H:
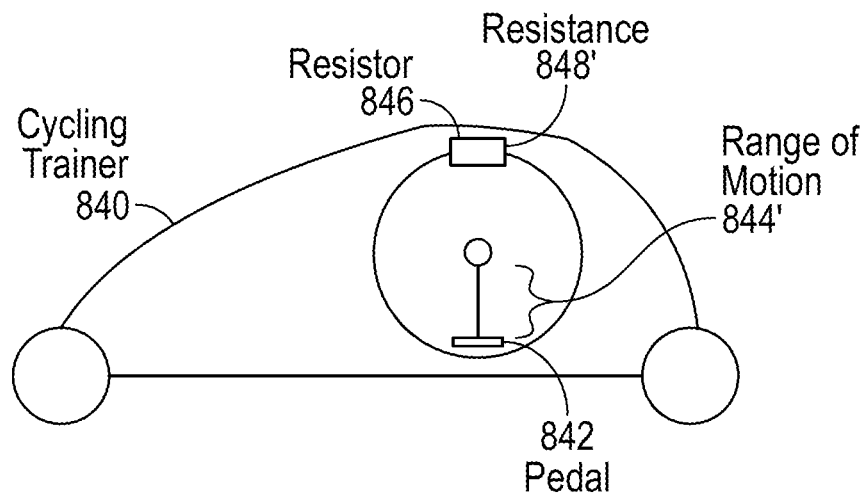

As shown in FIG. 8G, the patient may confirm that the discovery of the cycling trainer 840 is accurate. Alternatively, the patient may attempt to add other exercise trainers by utilizing the same approaches described in FIG. 8A for discovering other devices. In any case, as shown in FIG. 8H, the treatment utility interface 802 may display recommended settings (e.g., defined by the other parameters 729 of the modified treatment plan 720) for different components included on the cycling trainer 840. Again, the treatment utility interface 802 also permits the patient to modify/disable different settings (e.g., in a manner similar to that described in FIGS. 8C-8D).

When the patient approves the recommended settings, the patient interface 50 may cause the recommended settings to be applied to the cycling trainer 840. This may include, for example, changing the range of motion of the pedals 842 to four inches to establish a range of motion 844'. This may also include changing the resistor 846 to 35% to establish a resistance 848' against the pedals 842. This may further involve setting the workout duration to 7.5 minutes (e.g., using an internal clock on the cycling trainer 840 that causes the cycling trainer 840 to adjust its operation after 7.5 minutes have lapsed).

The components and configurable aspects of the cycling trainer 840 are exemplary; further, any cycling trainer may be utilized consistent with the scope of this disclosure. It is also noted that the embodiments set forth herein are not limited to cycling trainers and that all forms of exercise equipment, having varying adjustments and capabilities at any level of granularity, may be utilized consistent with the scope of this disclosure.

Additionally, it should be noted that the various settings described throughout FIGS. 8A-8H are not required to be static in nature throughout the duration of the treatment session. To the contrary, the modified treatment plan 720 may include information that enables one or more of the settings to change in response to conditions being satisfied. Such conditions may include, for example, an amount of time lapsing (e.g., five minutes after the treatment session starts), a milestone being hit (e.g., clinician/patient indicating a meditation period is been completed), an achievement being made (e.g., a low resting heart rate being hit), and the like.

The foregoing examples of settings, conditions, etc., are not meant to be limiting; further, any number and/or type of settings, conditions, etc., at any level of granularity, may be used to dynamically modify the modified treatment plan 720 consistent with the scope of this disclosure.

Figure 9:
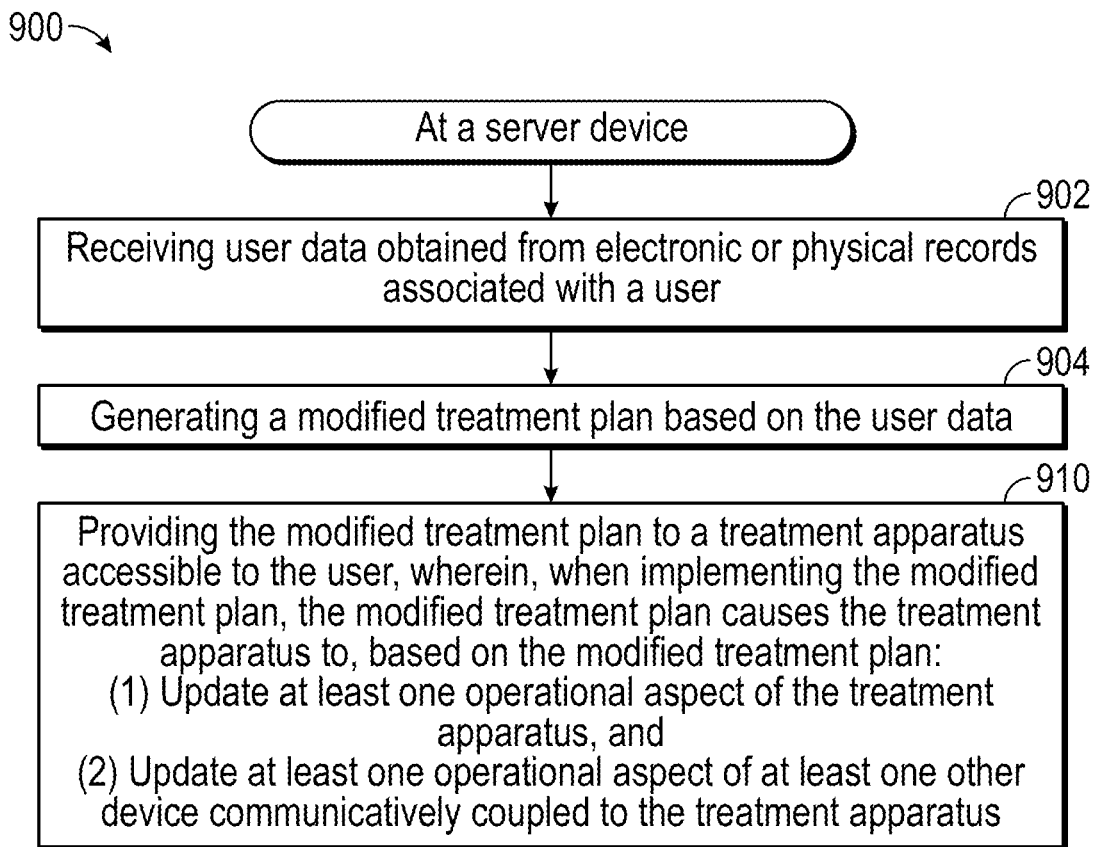
FIG. 9 shows an example embodiment of a method for implementing dynamic treatment environments, according to some embodiments.

FIG. 9 shows an example embodiment of a method 900 for implementing dynamic treatment environments, according to some embodiments. Method 900 includes operations performed by processors of a computing device (e.g., any component of FIG. 1, such as the server 30). In some embodiments, one or more operations of the method 900 are implemented in computer instructions stored on a memory device and executed by a processing device. The operations of the method 900 may be performed in some combination with any of the operations of any of the methods described herein.

Regarding the method 900, at 902, the processing device—e.g., the server 30—receives user data obtained from electronic or physical records associated with a user. At 904, the server 30 generates a modified treatment plan based on the user data obtained from electronic or physical records associated with the user. At 910, the server 30 provides the modified treatment plan to a treatment apparatus accessible to the user. In turn, when the treatment apparatus implements the modified treatment plan, the modified treatment plan causes the treatment apparatus to, based on the modified treatment plan: (1) update at least one operational aspect of the treatment apparatus, and (2) update at least one operational aspect of at least one other device communicatively coupled to the treatment apparatus.

Figure 10:
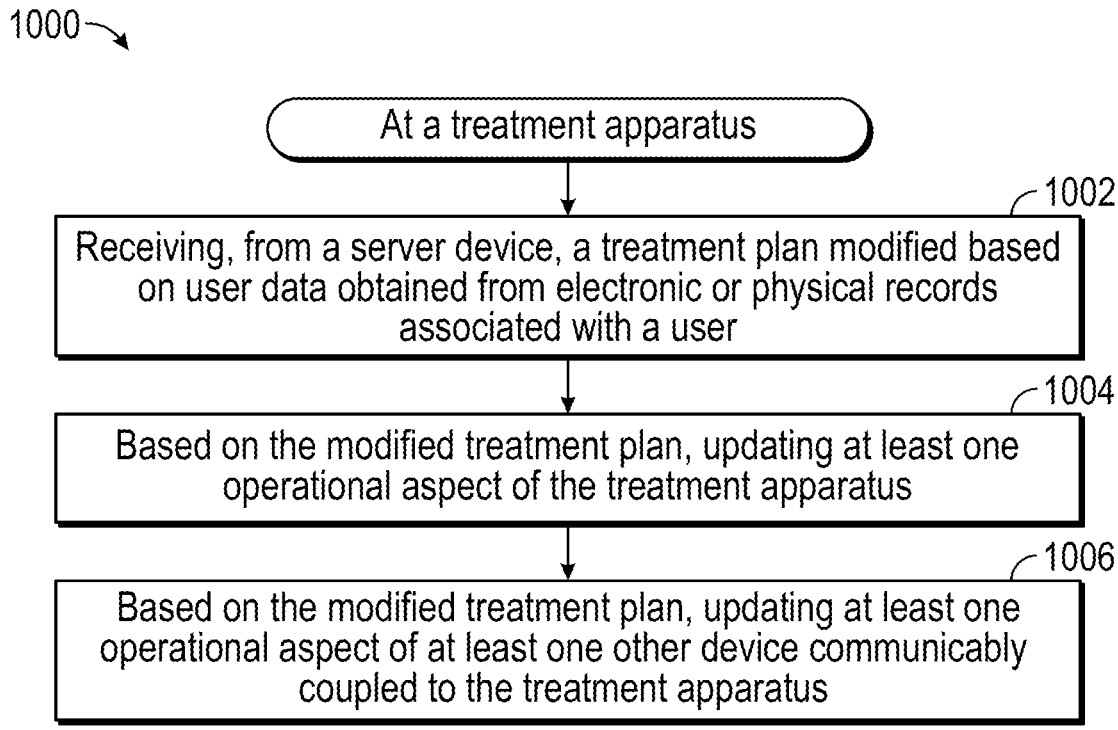
FIG. 10 shows an example embodiment of another method for implementing dynamic treatment environments, according to some embodiments.

FIG. 10 shows an example embodiment of another method 1000 for implementing dynamic treatment environments, according to some embodiments. Method 1000 includes operations performed by processors of a computing device (e.g., any component of FIG. 1, such as the patient interface 50, the treatment apparatus 70, and the like). In some embodiments, one or more operations of the method 1000 are implemented in computer instructions stored on a memory device and executed by a processing device. The operations of the method 1000 may be performed in some combination with any of the operations of any of the methods described herein.

Regarding the method 1000, at 1002, the processing device (e.g., a treatment apparatus) receives, from a server device (e.g., the server 30), a treatment plan modified based on user data obtained from electronic or physical records associated with a user. At 1004, the processing device updates at least one operational aspect of the treatment apparatus based on the modified treatment plan. At 1006, the processing device updates at least one operational aspect of at least one other device communicably coupled to the treatment apparatus.

Figure 11:
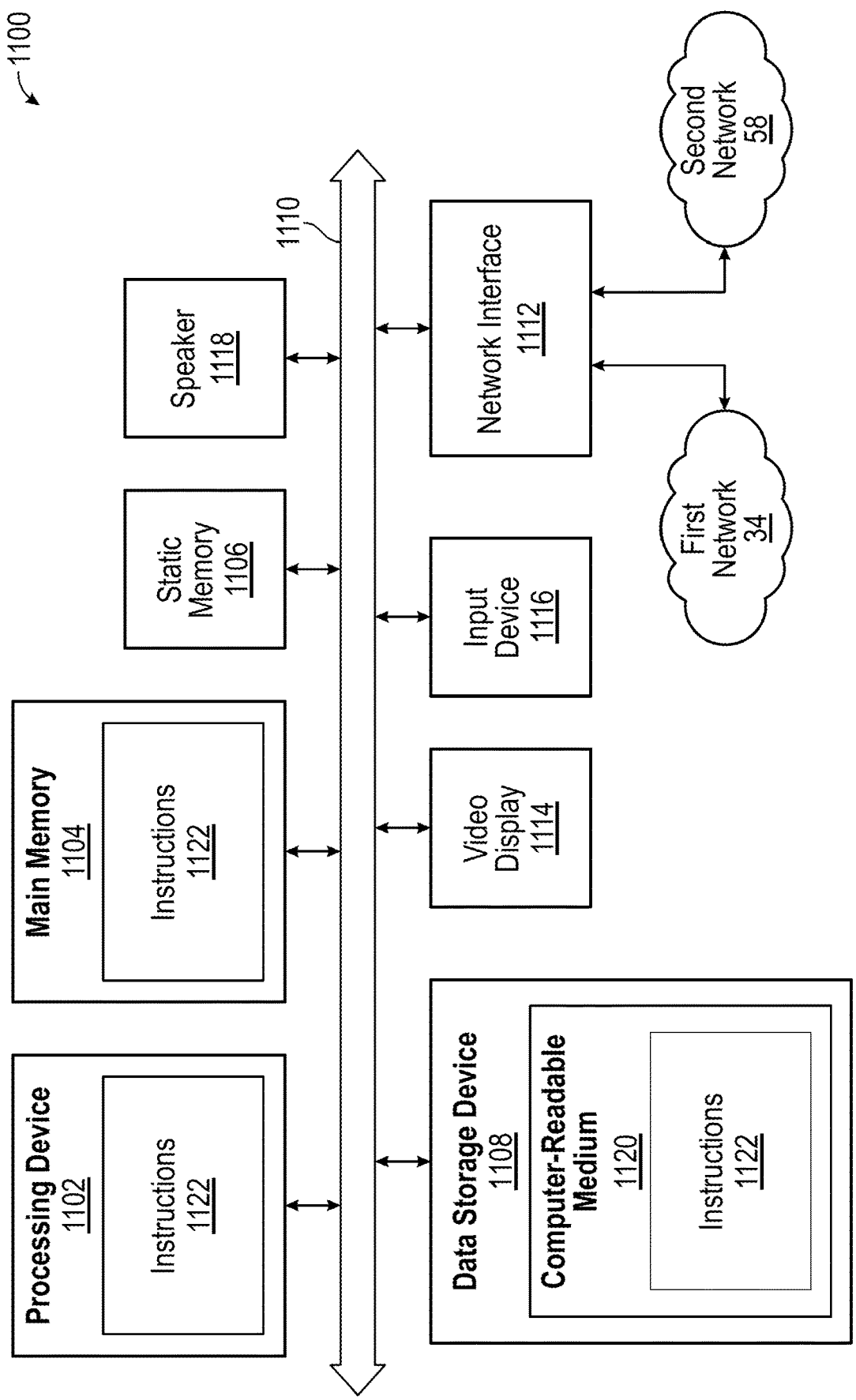
FIG. 11 shows an example computer system according to the present disclosure.

FIG. 11 shows an example computer system 1100 which can perform any one or more of the methods described herein, in accordance with one or more aspects of the present disclosure. In one example, computer system 1100 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1100 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1100 includes a processing device 1102, a main memory 1104 (e.g., read-only memory (ROM), flash memory, solid state drives (SSDs), dynamic random-access memory (DRAM) such as synchronous DRAM (SDRAM)), a static memory 1106 (e.g., flash memory, solid state drives (SSDs), static random-access memory (SRAM)), and a data storage device 1108, which communicate with each other via a bus 1110.

Processing device 1102 represents one or more general-purpose processing devices such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1100 may further include a network interface device 1112. The computer system 1100 also may include a video display 1114 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1116 (e.g., a keyboard and/or a mouse or a gaming-like control), and one or more speakers 1118 (e.g., a speaker). In one illustrative example, the video display 1114 and the input device(s) 1116 may be combined into a single component or device (e.g., an LCD touch screen).

The data storage device 1116 may include a computer-readable medium 1120 on which the instructions 1122 embodying any one or more of the methods, operations, or functions described herein is stored. The instructions 1122 may also reside, completely or at least partially, within the main memory 1104 and/or within the processing device 1102 during execution thereof by the computer system 1100. As such, the main memory 1104 and the processing device 1102 also constitute computer-readable media. The instructions 1122 may further be transmitted or received over a network via the network interface device 1112.

While the computer-readable storage medium 1120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding, or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for implementing dynamic treatment environments, the method comprising, at a server device:
  receiving user data obtained from records associated with a user;
  generating, based on the user data, a modified treatment; and
  sending, to a treatment apparatus accessible to the user, the modified treatment plan, wherein the modified treatment plan causes the treatment apparatus to:
    update at least one operational aspect of the treatment apparatus, and
    update at least one operational aspect of at least one other device communicatively coupled to the treatment apparatus.

Clause 2. The method of any clause herein, wherein the records contain one or more of:
  occupational characteristics of the user;
  health-related characteristics of the user;
  demographic characteristics of the user; or
  psychographic characteristics of the user.

Clause 3. The method of any clause herein, wherein updating the at least one operational aspect of the treatment apparatus comprises:
  updating a virtual background displayed on a display device communicatively coupled to the treatment apparatus, and
  updating notification settings on the treatment apparatus.

Clause 4. The method of any clause herein, wherein updating the notification settings comprises:
  causing the treatment apparatus to suppress at least one of audible, visual, haptic, or physical alerts, and
  causing the treatment apparatus to send all electronic communications directly to an alternative target comprising one of voicemail, text, email, or other alternative electronic receiver.

Clause 5. The method of any clause herein, wherein:
  the at least one other device comprises at least one light source, and
  updating the at least one operational aspect of the at least one light source comprises modifying one or more of a brightness or a color tone exhibited by at least one light source.

Clause 6. The method of any clause herein, wherein:
  the at least one other device comprises at least one audio component, and
  updating the at least one operational aspect of the at least one audio component comprises modifying one or more of an output volume or an audio stream played back by the at least one audio component.

Clause 7. The method of any clause herein, wherein the at least one audio component comprises at least one speaker or at least one amplifier communicably coupled to at least one speaker.

Clause 8. The method of any clause, wherein:
  the at least one other device comprises at least one other computing device, and
  updating the at least one operational aspect of the at least one other computing device comprises updating notification settings at the at least one other computing device.

Clause 9. The method of any clause herein, wherein:

the at least one other device comprises a training device that includes at least one pedal or handle and at least one component that exerts resistance against a rotational motion of the at least one pedal or handle; and updating the at least one operational aspect of the training device comprises:

adjusting a range of motion of the at least one pedal, and by way of the at least one component, adjusting an amount of resistance against the rotational motion of the at least one pedal or handle.

Clause 10. The method of any clause herein, wherein, prior to updating the at least one operational aspect of the at least one other device, the treatment apparatus discovers the at least one other device on an authorized network to which the treatment apparatus and the at least one other device are communicably coupled.

Clause 11. A tangible, non-transitory computer-readable medium storing instructions that, when executed, cause a processing device to:

receive user data obtained from records associated with a user;

generate a modified treatment plan based on the user data; and sending, to a treatment apparatus accessible to the user, the modified treatment plan, wherein the modified treatment plan causes the treatment apparatus to:

update at least one operational aspect of the treatment apparatus, and update at least one operational aspect of at least one other device communicatively coupled to the treatment apparatus.

Clause 12. The tangible, non-transitory computer-readable medium of any clause herein, wherein the records contain one or more occupational characteristics of the user;

health-related characteristics of the user;

demographic characteristics of the user; or psychographic characteristics of the user.

Clause 13. The tangible, non-transitory computer-readable medium of any clause herein, wherein updating the at least one operational aspect of the treatment apparatus comprises:

updating a virtual background displayed on a display device communicatively coupled to the treatment apparatus, and updating notification settings on the treatment apparatus.

Clause 14. The tangible, non-transitory computer-readable medium of any clause herein, wherein updating the notification settings comprises:

causing the treatment apparatus to suppress at least one of audible, visual, haptic, or physical alerts, and causing the treatment apparatus to send all electronic communications directly to an alternative target comprising one of voicemail, text, email, or other alternative electronic receiver.

Clause 15. The tangible, non-transitory computer-readable medium of any clause herein, wherein:

the at least one other device comprises at least one light source, and updating the at least one operational aspect of the at least one light source comprises modifying one or more of a brightness or a color tone exhibited by at least one light source.

Clause 16. The tangible, non-transitory computer-readable medium of any clause herein, wherein:

the at least one other device comprises at least one audio component, and updating the at least one operational aspect of the at least one audio component comprises modifying one or more of an output volume or an audio stream played back by the at least one audio component.

Clause 17. The tangible, non-transitory computer-readable medium of any clause herein, wherein:

the at least one other device comprises a training device that includes at least one pedal or handle and at least one component that exerts resistance against a rotational motion of the at least one pedal or handle; and updating the at least one operational aspect of the training device comprises:

adjusting a range of motion of the at least one pedal, and by way of the at least one component, adjusting an amount of resistance against the rotational motion of the at least one pedal or handle.

Clause 18. A system comprising:

a memory device storing instructions; and a processing device communicatively coupled to the memory device, wherein the processing device executes the instructions to:

receive user data obtained from records associated with a user;

generate a modified treatment plan based on the user data; and sending, to a treatment apparatus accessible to the user, the modified treatment plan, wherein the modified treatment plan causes the treatment apparatus to:

update at least one operational aspect of the treatment apparatus, and update at least one operational aspect of at least one other device communicatively coupled to the treatment apparatus.

Clause 19. The system of any clause herein, wherein the records contain one or more of:

occupational characteristics of the user;

health-related characteristics of the user;

demographic characteristics of the user; or psychographic characteristics of the user.

Clause 20. The system of any clause herein, wherein the records are further defined as one or more of electronic and physical records.

Clause 21. The system of any clause herein, wherein updating the at least one operational aspect of the treatment apparatus comprises:

updating a virtual background displayed on a display device communicatively coupled to the treatment apparatus, and updating notification settings on the treatment apparatus.

Clause 22. The system of any clause herein, wherein the at least one other device comprises at least one light source, and the at least one light source having at least one operational aspect.

Clause 23. The system of any clause herein, further comprising updating the at least one operational aspect of the at least one light source.

Clause 24. The system of any clause herein, further comprising modifying one or more of a brightness or a color tone exhibited by the at least one light source.

Clause 25. The system of any clause herein, wherein the at least one other device comprises at least one audio component having at least one operation aspect.

Clause 26. The system of any clause herein, further comprising updating the at least one operational aspect of the at least one audio component.

Clause 27. The system of any clause herein, further comprising modifying one or more of an output volume or an audio stream played back by the at least one audio component.

Clause 28. The system of any clause herein, wherein the at least one other device comprises a training device that includes at least one rotatable pedal or handle and at least one component that exerts resistance against a rotational motion of the at least one pedal or handle.

Clause 29. The system of any clause herein, wherein the training device has at least one operational aspect.

Clause 30. The system of any clause herein, wherein the at least one operational aspect of the training device comprises:

adjusting a range of motion of the at least one rotational pedal, and adjusting an amount of the exerted resistance against the rotational motion of the at least one pedal or handle.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A system comprising:
    a memory device storing instructions; and
    a processing device communicatively coupled to the memory device, wherein the processing device executes the instructions to:
        receive user data obtained from records associated with a user;
        generate a modified treatment plan based on the user data; and
        send, to a treatment apparatus accessible to the user, the modified treatment plan, wherein the modified treatment plan causes the treatment apparatus to:
            update at least one operational aspect of the treatment apparatus, and
            update at least one operational aspect of at least one other device communicatively coupled to the treatment apparatus,
    wherein updating the at least one operational aspect of the treatment apparatus comprises updating a virtual background displayed on a display device communicatively coupled to the treatment apparatus, and updating notification settings on the treatment apparatus,
    wherein the at least one other device comprises at least one light source, and the at least one light source has at least one operational aspect, the method further comprising:
        updating the at least one operational aspect of the at least one light source;
        modifying one or more of a brightness or a color tone exhibited by the at least one light source, wherein the at least one other device comprises at least one audio component having at least one operation aspect, the method further comprising:
        updating the at least one operational aspect of the at least one audio component; and
        modifying one or more of an output volume or an audio stream played back by the at least one audio component, wherein the treatment apparatus includes at least one rotatable pedal or handle and at least one component that exerts resistance against a rotational motion of the at least one pedal or handle.

2. The system of claim 1, wherein the records contain one or more of:
    occupational characteristics of the user;
    health-related characteristics of the user;
    demographic characteristics of the user; or
    psychographic characteristics of the user.

3. The system of claim 1, wherein the records are further defined as one or more of electronic and physical records.

4. The system of claim 1, wherein the treatment apparatus has at least one operational aspect.

5. The system of claim 4, wherein the at least one operational aspect of the treatment apparatus comprises:
    adjusting a range of motion of the at least one rotatable pedal, and
    adjusting an amount of the exerted resistance against the rotational motion of the at least one rotatable pedal or handle.

6. A method for implementing dynamic treatment environments, the method comprising, at a server device:
    receiving user data obtained from records associated with a user;
    generating, based on the user data, a modified treatment; and
    sending, to a treatment apparatus accessible to the user, the modified treatment plan, wherein the modified treatment plan causes the treatment apparatus to:
        update at least one operational aspect of the treatment apparatus, and
        update at least one operational aspect of at least one other device communicatively coupled to the treatment apparatus,
    wherein updating the at least one operational aspect of the treatment apparatus comprises updating a virtual background displayed on a display device communicatively coupled to the treatment apparatus, and updating notification settings on the treatment apparatus, and
    wherein updating the notification settings comprises causing the treatment apparatus to suppress at least one of audible, visual, haptic, or physical alerts, and causing the treatment apparatus to send at least some electronic communications directly to an alternative target comprising one of voicemail, text, email, or other alternative electronic receiver.

7. The method of claim 6, wherein the records contain one or more of:
    occupational characteristics of the user;
    health-related characteristics of the user;
    demographic characteristics of the user; or
    psychographic characteristics of the user.

8. The method of claim 6, wherein:
    the at least one other device comprises at least one light source, and
    updating the at least one operational aspect of the at least one light source
    comprises modifying one or more of a brightness or a color tone exhibited by the at least one light source.

9. The method of claim 6, wherein:
the at least one other device comprises at least one audio component, and
updating the at least one operational aspect of the at least one audio component comprises modifying one or more of an output volume or an audio stream played back by the at least one audio component.

10. The method of claim 9, wherein the at least one audio component comprises at least one speaker or at least one amplifier communicably coupled to the at least one speaker.

11. The method of claim 6, wherein:
the at least one other device comprises at least one other computing device, and
updating the at least one operational aspect of the at least one other computing device comprises updating notification settings at the at least one other computing device.

12. The method of claim 6, wherein:
the at least one other device comprises a training device that includes at least one pedal or handle and at least one component that exerts resistance against a rotational motion of the at least one pedal or handle; and
updating the at least one operational aspect of the training device comprises:
adjusting a range of motion of the at least one pedal, and
by way of the at least one component, adjusting an amount of resistance against the rotational motion of the at least one pedal or handle.

13. The method of claim 6, wherein, prior to updating the at least one operational aspect of the at least one other device, the treatment apparatus discovers the at least one other device on an authorized network to which the treatment apparatus and the at least one other device are communicably coupled.

14. A tangible, non-transitory computer-readable medium storing instructions that, when executed, cause a processing device to:
receive user data obtained from records associated with a user;
generate a modified treatment plan based on the user data; and
sending, to a treatment apparatus accessible to the user, the modified treatment plan, wherein the modified treatment plan causes the treatment apparatus to:
update at least one operational aspect of the treatment apparatus, and
update at least one operational aspect of at least one other device communicatively coupled to the treatment apparatus,
wherein updating the at least one operational aspect of the treatment apparatus comprises updating a virtual background displayed on a display device communicatively coupled to the treatment apparatus, and updating notification settings on the treatment apparatus,
wherein updating the notification settings comprises causing the treatment apparatus to suppress at least one of audible, visual, haptic, or physical alerts, and causing the treatment apparatus to send at least some electronic communications directly to an alternative target comprising one of voicemail, text, email, or other alternative electronic receiver.

15. The tangible, non-transitory computer-readable medium of claim 14, wherein the records contain one or more
occupational characteristics of the user;
health-related characteristics of the user;
demographic characteristics of the user; or
psychographic characteristics of the user.

16. The tangible, non-transitory computer-readable medium of claim 14, wherein:
the at least one other device comprises at least one light source, and
updating the at least one operational aspect of the at least one light source comprises modifying one or more of a brightness or a color tone exhibited by at least one light source.

17. The tangible, non-transitory computer-readable medium of claim 14, wherein:
the at least one other device comprises at least one audio component, and
updating the at least one operational aspect of the at least one audio component comprises modifying one or more of an output volume or an audio stream played back by the at least one audio component.

18. The tangible, non-transitory computer-readable medium of claim 14, wherein:
the at least one other device comprises a training device that includes at least one pedal or handle and at least one component that exerts resistance against a rotational motion of the at least one pedal or handle; and
updating the at least one operational aspect of the training device comprises:
adjusting a range of motion of the at least one pedal, and
by way of the at least one component, adjusting an amount of resistance against the rotational motion of the at least one pedal or handle.

* * * * *